(12) United States Patent
Chen et al.

(10) Patent No.: US 10,385,322 B2
(45) Date of Patent: Aug. 20, 2019

(54) MUTANT GLUTAMATE DEHYDROGENASE FOR THE CONVERSION OF HOMOSERINE INTO 4-HYDROXY-2-KETOBUTYRATE

(71) Applicant: METABOLIC EXPLORER, Saint Beauzire (FR)

(72) Inventors: Zhen Chen, Beijing (CN); Feng Geng, Hamburg (DE); An-Ping Zeng, Rosengarten (DE); Wanda Dischert, Vic-le-Comte (FR); Philippe Soucaille, Deyme (FR)

(73) Assignee: METABOLIC EXPLORER, Saint Beauzire (FR)

( * ) Notice: Subject to any disclaimer, the term of this patent is extended or adjusted under 35 U.S.C. 154(b) by 40 days.

(21) Appl. No.: 15/516,282

(22) PCT Filed: Oct. 2, 2015

(86) PCT No.: PCT/EP2015/072806
§ 371 (c)(1),
(2) Date: Mar. 31, 2017

(87) PCT Pub. No.: WO2016/050959
PCT Pub. Date: Apr. 7, 2016

(65) Prior Publication Data
US 2017/0240868 A1    Aug. 24, 2017

(30) Foreign Application Priority Data
Oct. 3, 2014   (EP) .................................. 14306564

(51) Int. Cl.
*C12N 1/20* (2006.01)
*C12N 9/06* (2006.01)
(Continued)

(52) U.S. Cl.
CPC ............. *C12N 9/0016* (2013.01); *C12N 1/20* (2013.01); *C12P 7/18* (2013.01); *C12P 7/42* (2013.01);
(Continued)

(58) Field of Classification Search
None
See application file for complete search history.

(56) References Cited

U.S. PATENT DOCUMENTS

2011/0294178 A1* 12/2011 Soucaille ................ C12N 9/88
435/158
2017/0240868 A1* 8/2017 Chen .................... C12N 9/0016

FOREIGN PATENT DOCUMENTS

EP           2540834 A1   1/2013
WO    WO 2005/038017 A2  4/2005
(Continued)

OTHER PUBLICATIONS

Carrier et al., "Library of synthetic 5' secondary structures to manipulate mRNA stability in *Escherichia coli*," Biotechnol Prog., vol. 15, No. 1, 1999 (Published on Web Jan. 9, 1999), pp. 58-64 (8 pages total).
(Continued)

*Primary Examiner* — Richard C Ekstrom
(74) *Attorney, Agent, or Firm* — Birch, Stewart, Kolasch & Birch, LLP

(57) ABSTRACT

The present invention concerns a method for the production of derivatives of 4-hydroxy-2-ketobutyrate chosen among 1,3-propanediol or 2,4-dihydroxybutyrate by culturing a genetically modified microorganism for the production of the desired derivative of 4-hydroxy-2-ketobutyrate, the microorganism further comprising a gene coding for a mutant glutamate dehydrogenase converting by deamination
(Continued)

L-homoserine into 4-hydroxy-2-ketobutyrate. The invention also concerns said genetically modified microorganism.

17 Claims, 4 Drawing Sheets

Specification includes a Sequence Listing.

(51) Int. Cl.
    *C12P 7/18*     (2006.01)
    *C12P 7/42*     (2006.01)

(52) U.S. Cl.
    CPC ............... *C12Y 104/01002* (2013.01); *C12Y 104/01003* (2013.01); *C12Y 104/01004* (2013.01)

(56) References Cited

FOREIGN PATENT DOCUMENTS

| WO | WO 2010/076324 A1 | 7/2010 |
|---|---|---|
| WO | WO 2011/106696 A2 | 9/2011 |
| WO | WO 2012/004247 A1 | 1/2012 |
| WO | WO 2014/009435 A1 | 1/2014 |

OTHER PUBLICATIONS

Celińska, "Debottlenecking the 1,3-propanediol pathway by metabolic engineering," Biotechnology Advances, vol. 28, No. 4, 2010 (available online Mar. 31, 2010), pp. 519-530.

Celińska, "Fully glycerol-independent microbial production of 1,3-propanediol via non-natural pathway: Paving the way to success with synthetic tiles," Biotechnology Journal, vol. 10, No. 2, Feb. 2015, pp. 242-243 (3 pages total).

Chen et al., "Protein design and engineering of a de novo pathway for microbial production of 1,3-propanediol from glucose," Biotechnology Journal, vol. 10, No. 2, Feb. 2015, pp. 284-289 (7 pages total).

Extended European Search Report, dated Mar. 24, 2015, for European Application No. 14306564.7.

International Search Report and Written Opinion of the International Searching Authority (Forms PCT/ISA/220, PCT/ISA/237 and PCT/ISA/210), dated Dec. 18, 2015, for International Application No. PCT/EP2015/072806.

Morris et al., "Automated docking using a Lamarckian genetic algorithm and an empirical binding free energy function," J. Comput. Chem., vol. 19, No. 14, 1998, pp. 1639-1662.

Šali et al., "Comparative protein modelling by satisfaction of spatial restraints," J. Mol. Biol., vol. 234, No. 3, 1993, pp. 779-815.

Salis, "The ribosome binding site calculator," Methods Enzymol., vol. 498, Chapter 2, 2011, pp. 19-42.

Saxena et al., "Microbial production of 1,3-propanediol: Recent developments and emerging opportunities," Biotechnology Advances, vol. 27, No. 6, 2009 (available online Aug. 4, 2009), pp. 895-913.

Segel, "Enzyme kinetics," John Wiley & Sons, May 1993, pp. 44-54 and 100-112.

Wang et al., "Alteration of the amino acid substrate specificity of clostridial glutamate dehydrogenase by site-directed mutagenesis of an active-site lysine residue," Protein Engineering, vol. 8, No. 2, Feb. 1995, pp. 147-152.

Wang et al., "Conversion of a glutamate dehydrogenase into methionine/norleucine dehydrogenase by site-directed mutagenesis," Eur. J. Biochem., vol. 268, No. 22, Nov. 2001, pp. 5791-5799.

\* cited by examiner

Figure 2a

```
sp|Escherichia          ------------------------------------MDQTYSLESFLNHVQKRD
sp|Bacteroides          ---------------------------------------MNIEKIMSSLEAKH
sp|Clostridium          --------------------------------------MSKYVDRVIAEVEKKY
sp|Homo                 MYRYLGEALLLSRAGPAALGSASADSAALLGWARGQPAAAPQPGLALAARRHYSEAVADR
sp|Prevotella           ---------------------------------------MKATEVIEKLKAKF
sp|Saccharomyces        ------------------------------------------------------------
sp|Neurospora           ------------------------------------------------------MSNL
sp|Schizosaccharomyces  -------------------------------------------------------MST
sp|Emericella           ------------------------------------------------------MSNL
sp|Giardia              ---------------------------------------MPAQTIEELIAVIKQRD
sp|Agaricus             -------------------------------------------------------MVL
sp|Penicillium          -----------------------------------------------------MMQNL
sp|Laccaria             -------------------------------------------------------MVL sp|Escherichia          PNQTEFAQAVR-----------EVMTTLW--PFLEQNPKYRQMSLLERLVEP-ERVIQF
sp|Bacteroides          PGESEYLQAVK-----------EVLLSIE--DIYNQHPEFEKSKIIERLVEP-DRIFTF
sp|Clostridium          ADEPEFVQTVE-----------EVLSSLG--PVVDAHPEYEEVALLERMVIP-ERVIEF
sp|Homo                 EDDPNFFKMVEGFFDRGASIVEDKLVEDLR--TRESEEQKRNRVRGILRIIKPCNHVLSL
sp|Prevotella           PGQPEYIQAVS-----------QVLGTIE--EEYNKHPEFEKANLIERLCVP-DRILQF
sp|Saccharomyces        MSEPEFQQAYE-----------EVVSSLEDSTLFEQHPEYRKV--LPIVSVP-ERIIQF
sp|Neurospora           PSEPEFEQAYK-----------ELAYTLENSSLFQKHPEYRTA--LTVASIP-ERVIQF
sp|Schizosaccharomyces  PYEPEFQQAYK-----------EIVGSIESSKLFEVHPELKRV--LPIISIP-ERVLEF
sp|Emericella           PVEPEFEQAYK-----------ELASTLENSTLFEQHPEYRRA--LQVVSVP-ERVIQF
sp|Giardia              GHMTEFRQAVE-----------EVVDSLK--VIFEREPKYIPI--FERMLEP-ERVIIF
sp|Agaricus             PHEPEFEQALH-----------ELETSLQ--PFLTTNPQYKKA--LEIIQVP-ERVLQF
sp|Penicillium          PFEPEFEQAYK-----------ELASTLENSTLFQKKPEYRKA--LQVVSVP-ERVIQF
sp|Laccaria             PVEPEYEQALS-----------ELQNSLK--PFLAANPDYEKA--LEIVQIP-ERVLQF sp|Escherichia          RVVWVDDRNQIQVNRAWRVQFSSAIG PYKGGM RFHPSVNLSILKFLGFEQTFKNALTTLP
sp|Bacteroides          RVTWVDDKGEVQTNLGYRVQFNNAIG PYKGGI RFHASVNLSILKFLGFEQTFKNALTTLP
sp|Clostridium          RVPWEDDNGKVHVNTGYRVQFNGAIG PYKGGL RFAPSVNLSIMKFLGFEQAFKDSLTTLP
sp|Homo                 SFPIRRDDGSWEVIEGYRAQHSQHRT PCKGGI RYSTDVSVDEVKALASLMTYKCAVVDVP
sp|Prevotella           RVSWVDDNGNVQTNLGYRVQHNNAIG PYKGGL RFHKSVNASILKFLAFEQTFKNSLTTLP
sp|Saccharomyces        RVTWENDKGEQEVAQGYRVQYNSAKG PYKGGL RFHPSVNLSILKFLGFEQIFKNSLTGLD
sp|Neurospora           RVVWEDDNGNVQVNRGYRVQFNSALG PYKGGL RLHPSVNLSILKFLGFEQIFKNALTGLS
sp|Schizosaccharomyces  RVTWEDDKGNCRVNTGYRVQFNSALG PYKGGL RFHPSVNLSILKFLGFEQIFKNALTGLP
sp|Emericella           RVVWENDKGEVQINRGYRVQFNSALG PYKGGL RFHPSVNLSILKFLGFEQIFKNALTGLN
sp|Giardia              RVPWMDDAGRINVNRGFRVQYNSALG PYKGGL RFHPSVNLSILKFLGFEQILKNSLTTLP
sp|Agaricus             RVTWEDDQGKPQVNRGFRVQYNSALG PYKGGL RLHPTVNLSILKFLGFEQTFKNALTGLS
sp|Penicillium          RVVWEDDKGQVQINRGYRVQFNSALG PYKGGL RFHPTVNLSILKFLGFEQIFKNALTGLN
sp|Laccaria             RVVWEDDQGKAQVNRGFRVQYNSALG PYKGGL RLHPSVNLSILKFLGFEQTFKNALTGLS sp|Escherichia          MGGGKGGSDFDPKGKSEGEVMRFCQALMTELYR--HLGADTDVPAGDIGVGGREVGFMAG
sp|Bacteroides          MGGGKGGSDFSPRGKSDAEIMRFCQAFMLELWR--HLGPDMDVPAGDIGVGGREVGYMFG
sp|Clostridium          MGGAKGGSDFDPNGKSDREVMRFCQAFMTELYR--HIGPDIDVPAGDLGVGAREIGYMYG
sp|Homo                 FGGAKAGVKINPKNYTDNELEKITRRFTMELAKKGFIGPGIDVPAPDMSTGEREMSWIAD
sp|Prevotella           MGGAKGGSDFDPHGKSDMEVMRFCQAFMNELYR---LIGPDEDVPAGDIGVGGREVGYMFG
sp|Saccharomyces        MGGGKGGLCVDLKGRSNNEIRRICYAFMRELSR--HIGQDTDVPAGDIGVGGREIGYLFG
sp|Neurospora           MGGGKGGADFDPKGKSDAEIRRFCCAFMAELHK--HIGADTDVPAGDIGVGGREIGYMFG
sp|Schizosaccharomyces  MGGGKGGSDFDPKGKSDNEIRRFSQAFMRQLFR--YIGPQTDVPAGDIGVTGFVVMHMFG
sp|Emericella           MGGGKGGSDFDPKGKSDSEIRRFCTAFMTELCK--HIGADTDVPAGDIGVTGREVGFLFG
sp|Giardia              MGGGKGGSDFDPKGKSDNEVMRFCQSFMTELQR--HVGADTDVPAGDIGVGAREIGYLYG
sp|Agaricus             MGGGKGGSDFDPKGKSDNEIRRFCVAFMSELFR--HIGQDTDVPAGDIGTGAREIGFLFG
sp|Penicillium          MGGGKGGSDFDPKGKTDNEIRRFCVSFMTELCK--HIGADTDVPAGDIGVTGREVGFMFG
sp|Laccaria             MGGGKGGSDFDPKGKSDGEIRRFCTSFMSELFR--HIGQDTDVPAGDIGTGAREIGYLFG
```

Figure 2b

```
sp|Escherichia         MMKKLSNNT-A----CVFTGKGLSFGGSLIRPEATGYGLVYFTEAMLKRHG----M----
sp|Bacteroides         MYKKLTREF-T----GTFTGKGLEFGGSLIRPEATGFGGLYFVNQMLQTKG----I----
sp|Clostridium         QYRKIVGGFYN----GVLTGKARSFGGSLVRPEATGYGSVYYVEAVMKHEN----D----
sp|Homo                TYASTIGHY-DINAHACVTGKPISQGGIHGRISATGRGVFHGIENFINEASYMSILGMTP
sp|Prevotella          QYKKLTHQF-Q----GILTGKGLEFGGSLIRPEATGYGNVYFLEDMLKTRG----E----
sp|Saccharomyces       AYRSYKNSW-E----GVLTGKGLNWGGSLIRPEATGYGLVYYTQAMIDYAT----NGKE-
sp|Neurospora          AYRKAANRF-E----GVLTGKGLSWGGSLIRPEATGYGLVYYVGHMLEYSG----AG---
sp|Schizosaccharomyces EYKRLRNEY-S----GVVTGKHMLTGGSNIRPEATGYGVVYYVKHMIEHRT----KGAE-
sp|Emericella          QYRRIRNQW-E----GVLTGKGGSWGGSLIRPEATGYGVVYYVEHMIKHVT----GGKE-
sp|Giardia             QYKRLRNEF-T----GVLTGKNVKWGGSFIRPEATGYGAVYFLEEMCKDNN----T----
sp|Agaricus            AYRRLKNEF-T----GMLTGKGINWGGSFIRPEATGYGLIYYVEHMIAHAC----PEYSL
sp|Penicillium         QYKKIRNQW-E----GVLTGKGGSWGGSLIRPEATGYGVVYYVEHMIQHAS----GGKE-
sp|Laccaria            AYKKLQNEF-V----GMLTGKGLAWGGSFIRPEATGYGLIYYVEHMIAKAA----PEYSL sp|Escherichia         GFEGMRVSVSGSGNVAQYAIEKAMEFGARVITASDSSGTVV--DESG-FTK-EKLARLIE
sp|Bacteroides         DIKGKTVAISGFGNVAWGAATKATELGAKVVTISGPDGYIY--DPNG-ISG-EKIDYMLE
sp|Clostridium         TLVGKTVALAGFGNVAWGAAKKLAELGAKAVTLSGPDGYIY--DPEG-ITTEEKINYMLE
sp|Homo                GFGDKTFVVQGFGNVGLHSMRYLHRFGAKCIAVGESDGSIW--NPDG-IDP---------
sp|Prevotella          SLEGKTVLVSGSGNVAQYTIEKLLQLGAKPVTCSDSNGYIY--DPDG-IDA-EKLAFIME
sp|Saccharomyces       SFEGKRVTISGSGNVAQYAALKVIELGGTVVSLSDSKGCII--SETG-ITS-EQVADISS
sp|Neurospora          SYAGKRVALSGSGNVAQYAALKLIELGATVVSLSDSKGALVATGESG-ITV-EDINAVMA
sp|Schizosaccharomyces TLKGKRVAISGSGNVAQYAALKCIQEGAIVKSISDSKGVLIAKTAEG-LVP-EEIHEIMA
sp|Emericella          SFAGKRVAISGSGNVAQYAALKVIELGGSVVSLSDSKGSLIVKDESASFTP-EEIALIAD
sp|Giardia             VIRGKNVLLSGSGNVAQFACEKLIQLGAKVLTFSDSNGTIV--DKDG-FNE-EKLAHLMY
sp|Agaricus            DRPSTLVAISGSGNVSQFTALKVIELGATVLSLSDSKGSLI--SEKG-YTK-EAIEKIAE
sp|Penicillium         SFAGKRVAISGSGNVAQYAALKVIELGGSVISLSDSQGALVLNGEEGSFTA-EEINTIAE
sp|Laccaria            SKPETLVAISGSGNVAQFTALKVIELGATVLSLSDSKGSLI--AEKG-YTK-EFIKEIGQ sp|Escherichia         IKASRDGRVADYAKEF------GLVYLEGQQPW--SL----PVDIALPCATQNELDVDAAH
sp|Bacteroides         LRASGNDIVAPYADEF------PGSTFVAGKRPW--EV----KADIALPCATQNELNGEDAK
sp|Clostridium         MRASGRNKVQDYADKF------GVQFFPGEKPW--GQ----KVDIIMPCATQNDVDLEQAK
sp|Homo                ------KELEDFKLQH------GSILGFPKAKPYEGSILEADCDILIPAASEKQLTKSNAP
sp|Prevotella          LKNVKRGRIKEYAEKY------GVKYVENARPW--GE----KADIATPCATQDEINEAEAK
sp|Saccharomyces       AKVNF-KSLEQIVNEYSTFSENKVQYIAGARPW--THV-QKVDIALPCATQNEVSGEEAK
sp|Neurospora          IKEAR-QSLTSFQHAG------HLKWIEGARPW--LHV-GKVDIALPCATQNEVSKEEAE
sp|Schizosaccharomyces LKEKR-ASIADSASLC------KKHHYIAGARPW--TNV-GEIDIALPCATQNEVSGEEAA
sp|Emericella          LKVAR-KQLSELATSSAF--AGKFTYIPDARPW--TNIPGKFEVALPSATQNEVSGEEAE
sp|Giardia             LKNEKRGRVSEFKDKY------PSVAYYEGKKPW--ECFEGQMDCIMPCATQNEVSGDDAT
sp|Agaricus            LKLKG-GALEAIVDDL------GAGYTYHAGKRPW--TLL-PQVHIALPCATQNEVSQEEAE
sp|Penicillium         IKVQR-KQIAELATQDAF--SSKFKYIPGARPW--TNIAGRIDVALPSATQNEVSGDEAK
sp|Laccaria            LKLKG-GALESLAQRE------GYTYHAGKRPW--SLL-PVVHVALPGATQNEVSKTEAE sp|Escherichia         QLIANGVKAVAEGANMPTTIEATELFQQA---------GVLFAPGKAANAGGVATSGLEM
sp|Bacteroides         NLIDNNVLCVGEISNMGCTPEAIDLFIEH---------KTMYAPGKAVNAGGVATSGLEM
sp|Clostridium         KIVANNVKYYIEVANMPTTNEALRFLMQQP--------NMVVAPSKAVNAGGVLVSGFEM
sp|Homo                RVKA---KIIAEGANGPTTPEADKIFLER---------NIMVIPDLYLNAGGVTVSYFEW
sp|Prevotella          TLIANGVFAVSEGANMPTEPAAIKVFQDA---------KILYCPGKASNAGGVATSGLEM
sp|Saccharomyces       ALVAQGVKFIAEGSNMGSTPEAIAVFETARSTATGPSEAVWYGPPKAANLGGVAVSGLEM
sp|Neurospora          GLLAAGCKFVAEGSNMGCTLEAIEVFENNRKEKKG--EAVWYAPGKAANCGGVAVSGLEM
sp|Schizosaccharomyces ALIKQGCRYVAEGSNMGSSAEAVEVFEKSRASGE----GCWLAPGKAANAGGVAVSGLEM
sp|Emericella          HLIKSGVRYIAEGSNMGCTQAAIDIFEAHRNANPG--DAIWYAPGKAANAGGVAVSGLEM
sp|Giardia             RLVGLGLKFVAEGANMPSTAEAVHVYHAK---------GVMYGPAKASNAGGVSVSGLEM
sp|Agaricus            ALVKAGTRIVAEGSNMGCTEEAIAIFENSRRASRA---GVWYAPGKASNCGGVAVSGLEM
sp|Penicillium         ALIAAGCKFIAEGSNMGSTQEAIDVFEAHRDANPG--AAAIWYAPGKAANAGGVAVSGLEM
sp|Laccaria            DLIKAGVRIVAEGSNMGCTEDAIAVFEASRKAGAG--GVWYAPGKASNCGGVAVSGLEM
```

Figure 2c

```
sp|Escherichia        AQNAARLGWKA-----EKVDARLHHIM-----------------------------------
sp|Bacteroides        SQNAMHLSWSA-----AEVDEKLHSIM-----------------------------------
sp|Clostridium        SQNSERLSWTA-----EEVDSKLHQVM-----------------------------------
sp|Homo               LKNLNHVSYGRLTFKYERDSNYHLLMSVQESLERKFGKHGGTIPIVPTAEFQDRISGASE
sp|Prevotella         SQNSERLSWTR-----EEVDTKLHNIM-----------------------------------
sp|Saccharomyces      AQNSQRITWTS-----ERVDQELKRIM-----------------------------------
sp|Neurospora         AQNSQRLNWTQ-----AEVDEKLKDIM-----------------------------------
sp|Schizosaccharomyces AQNAQFSTWTH----AEVDAKLAGIM-----------------------------------
sp|Emericella         AQNSARLSWTS-----EEVDARLKGIM-----------------------------------
sp|Giardia            SQNSVRLQWTA-----EEVDQKLRGIM-----------------------------------
sp|Agaricus           AQNSQRLAWST-----QEVDAKLKSIM-----------------------------------
sp|Penicillium        AQNSARVNWSR-----EEVDSRLKKIM-----------------------------------
sp|Laccaria           AQNSQRLAWTT-----DQVDQKLKKIM----------------------------------- sp|Escherichia        LDIHHACVEHG----------GEGE-------QTNYVQGANIAGFVKVADAMLAQGVI----
sp|Bacteroides        HGIHAQCVKYG--------TEPDGY-------INYVKGANIAGFMKVAHAMMGQGII----
sp|Clostridium        TDIHDGSAAAAERY-------GLGY---------NLVAGANIVGFQKIADAMMAQGIAW---
sp|Homo               KDIVHSGLAYTMERSARQIMRTAMKYNLGLDLRTAAYVNAIEKVFKVYNEAGVTFT--
sp|Prevotella         DEIHANCVKYG--------TEPDGY-------INYVKGANVAGFMKVAKAMMAQGIY----
sp|Saccharomyces      INCFNECIDYAKKYT-----KDGK------VLPSLVKGANIASFIKVSDAMFDQGDVF---
sp|Neurospora         KNAFFNGLNTAKTYV--EAAEGE--------LPSLVAGSNIAGFVKVAQAMHDQGDWWSKN
sp|Schizosaccharomyces QNIFEQSTDVASKYC--DSGSNN-------IPSLVDGANIAGFLKVATAMQAVGDWW---
sp|Emericella         EDCFKNGLETAQKFA--TPAKGV--------LPSLVTGSNIAGFTKVAEAMKDQGDWW---
sp|Giardia            RGIFVACRDTAKKY---------GH------PKNYQMGANIAGFLKVADSMIEQGCV----
sp|Agaricus           AECYQICYTAGSRWSGEKVAEGVAEGEALPSLLSGANLAGFIKVADAMKEQGDWW---
sp|Penicillium        EDCFNNGLSTAKEYV--TPAEGV--------LPSLVAGSNIAGFTKVAEAMKEHGDWW---
sp|Laccaria           AECYEICLSAGTKWSGEEIKDGV--------LPSLLSGANVAGFIKVADAMREHGDWW---
```

MUTANT GLUTAMATE DEHYDROGENASE FOR THE CONVERSION OF HOMOSERINE INTO 4-HYDROXY-2-KETOBUTYRATE

DOMAIN OF THE INVENTION

The present invention relates to a method for the production of derivatives of 4-hydroxy-2-ketobutyrate chosen among 1,3-propanediol or 2,4-dihydroxybutyrate by culturing a genetically modified microorganism for the production of the desired derivative of 4-hydroxy-2-ketobutyrate, the microorganism further comprising a gene coding for a mutant glutamate dehydrogenase converting by deamination L-homoserine into 4-hydroxy-2-ketobutyrate. The invention also concerns said genetically modified microorganism.

BACKGROUND

Methods for the biosynthesis of derivatives of 4-hydroxy-2-ketobutyrate by fermentation, where the microorganism metabolically transforms a simple source of carbon into derivatives of 4-hydroxy-2-ketobutyrate are known in the art. Such derivatives of 4-hydroxy-2-ketobutyrate are in particular 1,3-propanediol or 2,4-dihydroxybutyrate. The latter is a precursor of methionine hydroxyl analogue (MHA).

Preparation of 1,3-propanediol from 4-hydroxy-2-ketobutyrate by fermentation is well disclosed in WO 2010/076324 and WO 2012/004247 patent applications which are incorporated herein by reference.

Preparation of 2,4-dihydroxybutyrate from 4-hydroxy-2-ketobutyrate by fermentation is well disclosed in WO 2014/009435 patent application incorporated herein by reference.

In these pathways of production of 1,3-propanediol or 2,4-dihydroxybutyrate, 4-hydroxy-2-ketobutyrate is obtained by the oxidative deamination of L-homoserine.

It is particularly known from these applications to improve the metabolic pathway to favour the production of L-homoserine and to limit the usual metabolic pathways using L-homoserine as a substrate, like for its conversion into L-threonine.

In patent applications WO 2010/076324 and WO 2012/004247, conversion of 4-hydroxy-2-ketobutyrate into 1,3-propanediol or into 2,4-dihydroxybutyrate are well described. The pathway for 1,3-propanediol production from 4-hydroxy-2-ketobutyrate comprises two steps after the conversion of L-homoserine into 4-hydroxy-2-ketobutyrate:
  a first step of converting 4-hydroxy-2-ketobutyrate into 3-hydroxypropionaldehyde, and
  a second step of converting 3-hydroxypropionaldehyde into 1,3-propanediol.

For 2,4-dihydroxybutyrate production, L-homoserine is converting into 4-hydroxy-2-ketobutyrate and then 4-hydroxy-2-ketobutyrate is converting into 2,4-dihydroxybutyrate as disclosed in patent application WO2014/009435.

Even if main steps of these pathways are well described, the step of converting L-homoserine into 4-hydroxy-2-ketobutyrate is a limiting step.

The inventors have now found that this step can be improved by using a mutant glutamate dehydrogenase converting L-homoserine into 4-hydroxy-2-ketobutyrate by deamination.

BRIEF DESCRIPTION OF THE INVENTION

The present invention concerns a method for the production of derivatives of 4-hydroxy-2-ketobutyrate chosen among 1,3-propanediol or 2,4-dihydroxybutyrate by culturing a genetically modified microorganism for the production of the desired derivative of 4-hydroxy-2-ketobutyrate, wherein the genetically modified microorganism further comprises a gene coding for a mutant glutamate dehydrogenase converting by deamination L-homoserine into 4-hydroxy-2-ketobutyrate and wherein said mutant glutamate dehydrogenase comprises at least one mutation where amino acid K (Lys) at position 92, by reference to *E. coli* glutamate dehydrogenase of SEQ ID NO: 1, is replaced by a non-polar amino acid.

The invention also concerns a genetically modified microorganism for the production of the desired derivative of 4-hydroxy-2-ketobutyrate and comprising a gene coding for a mutant glutamate dehydrogenase converting by deamination L-homoserine into 4-hydroxy-2-ketobutyrate as defined above.

The microorganism is selected among the group consisting of bacterium, yeast and fungus, particularly selected among Enterobacteriaceae, Clostridiaceae, Bacillaceae, Streptomycetaceae and Corynebacteriaceae. In a preferred embodiment, the microorganism is *Escherichia coli*.

DRAWINGS

FIG. 2 represents an alignment of several glutamate dehydrogenases.

DETAILED DESCRIPTION OF THE INVENTION

Figure 1:
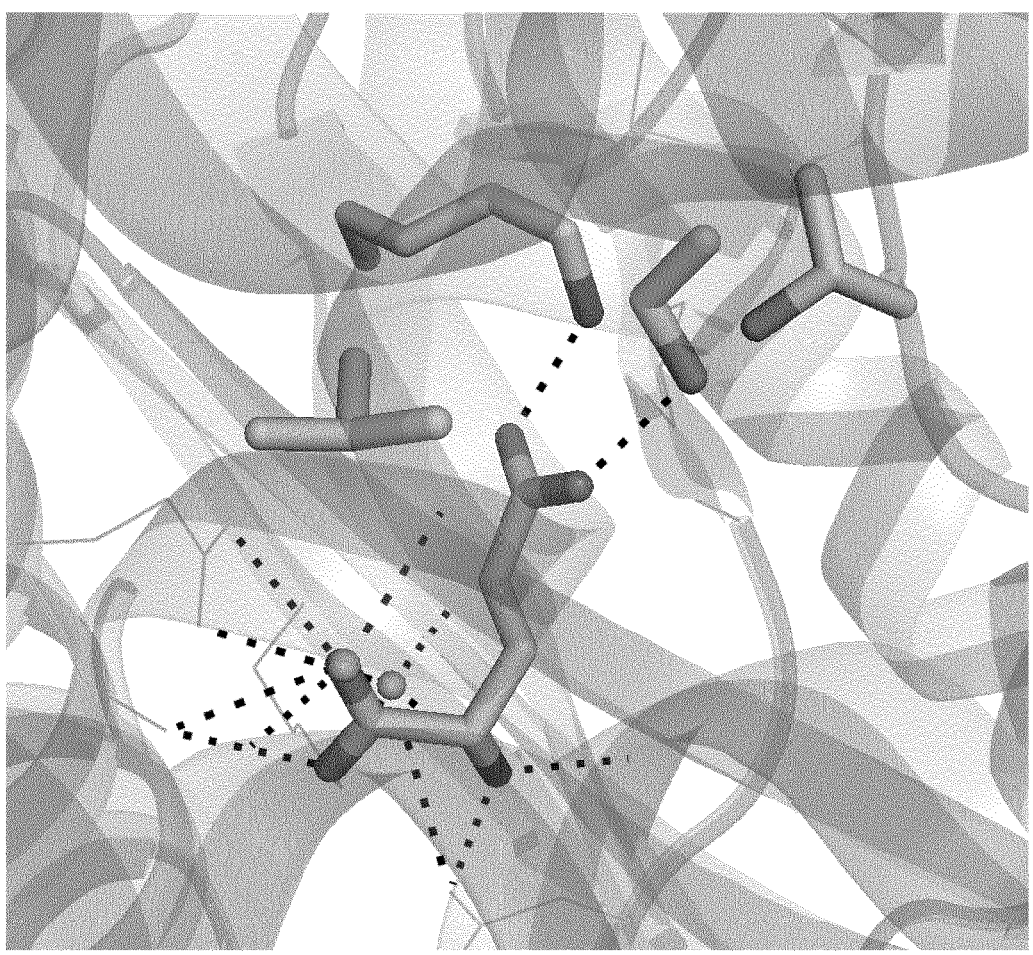
FIG. 1 represents a schematic view of molecular modeling of the active sites of *E. coli* glutamate dehydrogenase.

Before describing the present invention in detail, it is to be understood that this invention is not limited to particularly exemplified methods and may, of course, vary. It is also to be understood that the terminology used herein is for the purpose of describing particular embodiments of the invention only, and is not intended to be limiting, which will be limited only by the appended claims.

All publications, patents and patent applications cited herein, whether supra or infra, are hereby incorporated by reference in their entirety.

Furthermore, the practice of the present invention employs, unless otherwise indicated, conventional microbiological and molecular biological techniques within the skill of the art. Such techniques are well known to the skilled worker, and are explained fully in the literature.

It must be noted that as used herein and in the appended claims, the singular forms "a", "an", and "the" include plural reference unless the context clearly dictates otherwise. Thus, for example, a reference to "a microorganism" includes a plurality of such microorganisms, and a reference to "an endogenous gene" is a reference to one or more endogenous genes, and so forth. Unless defined otherwise, all technical and scientific terms used herein have the same meanings as commonly understood by one of ordinary skill in the art to which this invention belongs. Although any materials and methods similar or equivalent to those described herein can be used to practice or test the present invention, the preferred materials and methods are now described.

In the claims that follow and in the consecutive description of the invention, except where the context requires otherwise due to express language or necessary implication, the word "comprise", "contain", "involve" or "include" or variations such as "comprises", "comprising", "containing", "involved", "includes", "including" are used in an inclusive sense, i.e. to specify the presence of the stated features but not to preclude the presence or addition of further features in various embodiments of the invention.

The present invention concerns a method for the production of derivatives of 4-hydroxy-2-ketobutyrate chosen among 1,3-propanediol or 2,4-dihydroxybutyrate by culturing a genetically modified microorganism for the production of the desired derivative of 4-hydroxy-2-ketobutyrate, wherein the genetically modified microorganism further comprises a gene coding for a mutant glutamate dehydrogenase converting by deamination L-homoserine into 4-hydroxy-2-ketobutyrate and wherein said mutant glutamate dehydrogenase comprises at least one mutation where amino acid K (Lys) at position 92, by reference to *E. coli* glutamate dehydrogenase of SEQ ID NO: 1, is replaced by a non polar amino acid.

The terms "derivatives of 4-hydroxy-2-ketobutyrate" thus refer to products of conversion of 4-hydroxy-2-ketobutyrate after one or two steps of conversion of 4-hydroxy-2-ketobutyrate.

The term "microorganism", as used herein, refers to a bacterium, yeast or fungus which is not modified artificially. Preferentially, the microorganism is selected among Enterobacteriaceae, Bacillaceae, Corynebacteriaceae, Clostridiaceae, Streptomycetaceae and yeast. More preferentially the microorganism is a species of *Escherichia, Klebsiella, Thermoanaerobacterium, Corynebacterium, Clostridium* or *Saccharomyces*. More preferentially the microorganism is selected among *Escherichia coli, Klebsiella pneumoniae, Thermoanaerobacterium Thermosaccharolyticum, Corynebacterium glutamicum, Clostridium sphenoides* or *Saccharomyces cerevisiae*. Even more preferentially the microorganism of the invention is *Escherichia coli*.

The term "recombinant microorganism" or "genetically modified microorganism", as used herein, refers to a bacterium, yeast or fungus that is not found in nature and is genetically different from its equivalent found in nature. It means it is modified either by introduction or by deletion or by modification of genetic elements. It can also be transformed by forcing the development and evolution of new metabolic pathways by combining directed mutagenesis and evolution under specific selection pressure (see, for example, WO2005/073364 or WO2008/116852).

A microorganism genetically modified for the production of 1,3-propanediol means according to the invention a microorganism comprising a modified metabolic pathway allowing the conversion of a source of carbon into 1,3-propanediol when the microorganism of the invention is cultured on a culture medium comprising said source of carbon as sole source of carbon.

A microorganism genetically modified for the production of 2,4-dihydroxybutyrate means according to the invention a microorganism comprising a modified metabolic pathway allowing the conversion of a source of carbon into 2,4-dihydroxybutyrate when the microorganism of the invention is cultured on a culture medium comprising said source of carbon as sole source of carbon.

The term 'deamination', as used herein, refers to the removal of an amine group from one molecule. In the context of the invention the deamination refers to the removal of the amine group from L-homoserine in order to form 4-hydroxy-2-ketobutyrate compound by releasing ammonia in the process.

A microorganism may be modified to express exogenous genes if these genes are introduced into the microorganism with all the elements allowing their expression in the host microorganism. The modification or "transformation" of microorganisms with exogenous DNA is a routine task for those skilled in the art.

A microorganism may be modified to modulate the expression level of an endogenous gene.

The term "endogenous gene" means that the gene was present in the microorganism before any genetic modification. Endogenous genes may be overexpressed by introducing heterologous sequences in addition to, or to replace endogenous regulatory elements, or by introducing one or more supplementary copies of the gene into the chromosome or a plasmid. Endogenous genes may also be modified to modulate their expression and/or activity. For example, mutations may be introduced into the coding sequence to modify the gene product or heterologous sequences may be introduced in addition to or to replace endogenous regulatory elements. Modulation of an endogenous gene may result in the up-regulation and/or enhancement of the activity of the gene product, or alternatively, down regulate and/or lower the activity of the endogenous gene product.

Another way to modulate their expression is to exchange the endogenous promoter of a gene (e.g., wild type promoter) with a stronger or weaker promoter to up or down regulate expression of the endogenous gene. These promoters may be homologous or heterologous. It is well within the ability of the person skilled in the art to select appropriate promoters.

Contrariwise, "exogenous gene" or "heterologous gene" means that the gene was introduced into a microorganism, by means well known by the man skilled in the art whereas this gene is not naturally occurring in the microorganism. Exogenous genes may be integrated into the host chromosome, or be expressed extra-chromosomally by plasmids or vectors. A variety of plasmids, which differ with respect to their origin of replication and their copy number in the cell, are well known in the art. "Overexpression" or "overexpressing" is also used to designate expression of exogenous genes in the microorganisms.

In the context of the invention, the term "homologous gene" is not limited to designate genes having a theoretical common genetic ancestor, but includes genes which may be genetically unrelated that have, none the less, evolved to encode protein which perform similar functions and/or have similar structure. Therefore the term 'functional homolog" for the purpose of the present invention relates to the fact that a certain enzymatic activity may not only be provided by a specific protein of defined amino acid sequence, but also by proteins of similar sequence from other (un)related microorganisms.

Using the references given in Uniprot for known protein or in Genbank for known genes, those skilled in the art are able to obtain protein and/or gene sequences and to determine the equivalent genes in other organisms, bacterial strains, yeast, fungi, mammals, plants, etc. This routine work is advantageously done using consensus sequences that can be determined by carrying out sequence alignments with genes derived from other microorganisms and designing degenerate probes to clone the corresponding gene in another organism. These routine methods of molecular biology are well known to those skilled in the art.

The microorganism may also be modified to increase or decrease the activity of one or more proteins.

Increasing an activity can be obtained by improving the protein catalytic efficiency or decreasing protein turnover or decreasing messenger RNA (mRNA) turnover or increasing transcription of the gene or increasing translation of the mRNA.

Improving the protein catalytic efficiency means increasing the kcat and/or decreasing the Km for a given substrate and/or a given cofactor, and/or increasing the Ki for a given inhibitor. kcat, Km and Ki are Michaelis-Menten constants that the man skilled in the art is able to determine (Segel, 1993). Decreasing protein turnover means stabilizing the protein. Methods to improve protein catalytic efficiency and/or decrease protein turnover are well known from the man skilled in the art. Those include rational engineering with sequence and/or structural analysis and directed mutagenesis, as well as random mutagenesis and screening. Mutations can be introduced by site-directed mutagenesis by usual methods like Polymerase Chain Reaction (PCR), or by random mutagenesis techniques, such as use of mutagenic agents (Ultra-Violet rays or chemical agents like nitrosoguanidine (NTG) or ethylmethanesulfonate (EMS)) or use of PCR techniques (DNA shuffling or error-prone PCR). Stabilizing the protein can also be achieved by adding a peptide sequence called "tag" either at the N-terminus or the C-terminus of the protein. Tags are well known from the man skilled in the art. For instance, a Glutathione-S-Transferase (GST) can be used to stabilize a protein.

Decreasing mRNA turnover can be achieved by modifying the gene sequence of the 5'-untranslated region (5'-UTR) and/or the coding region, and/or the 3'-UTR (Carrier and Keasling, 1999).

Increasing transcription of a gene can be achieved by increasing the number of copies of the gene and/or using a promoter leading to a higher level of expression of the gene. "Overexpression" or "overexpressing" is also used to designate increasing transcription of a gene in the microorganisms.

For increasing the number of copies of the gene in the microorganism, the gene is encoded chromosomally or extrachromosomally. When the gene is located on the chromosome, several copies of the gene can be introduced on the chromosome by methods of recombination, known by the expert in the field (including gene replacement). When the gene is located extra-chromosomally, it may be carried by different types of plasmids that differ with respect to their origin of replication and thus their copy number in the cell. These plasmids are present in the microorganism in 1 to 5 copies, or about 20 copies, or up to 500 copies, depending on the nature of the plasmid: low copy number plasmids with tight replication (e.g for *E. coli* pSC101, RK2), low copy number plasmids (e.g for *E. coli* pACYC, pRSF1010) or high copy number plasmids (e.g for *E. coli* pSK bluescript II).

For using a promoter leading to a high level of expression of the gene the man skilled in the art knows which promoters are the most convenient, for example promoters Ptrc, Ptac, Plac, or the lambda promoter $P_R$ and $P_L$ are widely used. These promoters can be "inducible" by a particular compound or by specific external condition like temperature or light. These promoters may be homologous or heterologous.

Increasing translation of the mRNA can be achieved by modifying the Ribosome Binding Site (RBS). A RBS is a sequence on mRNA that is bound by the ribosome when initiating protein translation. It can be either the 5' cap of a mRNA in eukaryotes, a region 6-7 nucleotides upstream of the start codon AUG in prokaryotes (called the Shine-Dalgarno sequence), or an internal ribosome entry site (IRES) in viruses. By modifying this sequence, it is possible to change the protein translation initiation rate, proportionally alter its production rate, and control its activity inside the cell. The same RBS sequence will not have the same impact according to the nature of the mRNA. It is possible to optimize the strength of a RBS sequence to achieve a targeted translation initiation rate by using the software RBS CALCULATOR (Salis, 2011).

The man skilled in the art knows different means and method to measure ribonucleic acid concentration or protein concentration in the cell including for instance use of Reverse Transcription Polymerase Chain Reaction (RT-PCR) and Real-time Polymerase Chain Reaction (qPCR) to determine ribonucleic acid concentration and use of specific antibody to determine concentration of specific protein.

Decreasing the activity of an enzyme means either decreasing its specific catalytic activity by mutating the gene so as to change the amino acid sequence and/or decreasing concentrations of the protein in the cell by mutating the nucleotidic sequence or by deleting the coding region of the gene.

The man skilled in the art knows different means and method to measure ribonucleic acid concentration or protein concentration in the cell including for instance use of Reverse Transcription Polymerase Chain Reaction (RT-PCR) and Real-time Polymerase Chain Reaction (qPCR) to determine ribonucleic acid concentration and use of specific antibody to determine concentration of specific protein.

Microorganisms genetically modified for the production of derivatives of 4-hydroxy-2-ketobutyrate chosen among 1,3-propanediol and 2,4-dihydroxybutyrate comprising a metabolic pathway for the conversion of 4-hydroxy-2-ketobutyrate into its desired derivative are known in the art.

In a particular embodiment of the invention, the genetically modified microorganism for the production of the desired derivative of 4-hydroxy-2-ketobutyrate is modified for the production of 1,3-propanediol from 4-hydroxy-2-ketobutyrate. This modified microorganism is particularly described in WO 2010/076324 and WO 2012/004247, incorporated herein by reference.

The metabolic pathway for the conversion of 4-hydroxy-2-ketobutyrate into 1,3-propanediol is preferably a two-steps pathway comprising:
  conversion of 4-hydroxy-2-ketobutyrate into 3-hydroxypropionaldehyde, and
  conversion of 3-hydroxypropionaldehyde into 1,3-propanediol.

Preferably, the method of production according to the present invention is performed with a microorganism, particularly a bacterium, which contains at least one gene encoding an enzyme with 2-keto acid decarboxylase activity for the conversion of 4-hydroxy-2-ketobutyrate into 3-hydroxypropionaldehyde and at least one gene encoding an enzyme with hydroxy aldehyde reductase activity for the conversion of 3-hydroxypropionaldehyde into 1,3-propanediol. Those genes can be exogenous or endogenous, and can be expressed chromosomally or extrachromosomally.

Genes coding for a 2-keto acid decarboxylase activity are known in the art, including Pdc genes from various species, and more particularly the Pdc1, Pdc5, Pdc6, Aro10 and Thi3 genes from *Saccharomyces cerevisiae*, kivD gene from *Lactococcus lactis*, pdc gene from *Clostridium acetobutylicum*, Pdc2 and Pdc3 genes from *Arabidopsis thaliana*, Pdc1, Pdc2 and Aro10 genes from *Pichia stipitis*; pdc gene from *Zymomonas mobilis*. The first subunit of the 2-ketoglutarate decarboxylase complex, encoded by the gene sucA from *Escherichia coli*, also possesses 2-keto acid decarboxylase activity, as well as the enzyme encoded by the gene dxs of *Escherichia coli*. Functional homologues, functional variants and functional fragments of said genes and proteins are encompassed by the definition.

Genes coding for a hydroxy aldehyde reductase activity are also well known in the art, including the yqhD, fucO, dkgA, dkgB genes from *Escherichia coli* and the ADH1 and ADH2 genes from *Saccharomyces cerevisiae*. Functional homologues, functional variants and functional fragments of said genes and proteins are encompassed by the definition.

In a preferred embodiment, the genetically modified microorganism expressed at least one of the following genes: at least one gene coding for a 2-keto acid decarboxylase activity and selected among kivD gene from *Lactococcus lactis* and pdc gene from *Zymomonas mobilis* and at least one gene coding for a hydroxy aldehyde reductase activity selected among ydhD gene from *Escherichia coli*.

In a further preferred embodiment, the genetically modified microorganism for the production of 1,3-propanediol from 4-hydroxy-2-ketobutyrate is selected among *Escherichia coli*, overexpressing pdc gene from *Zymomonas mobilis* and yqhD gene from *Escherichia coli*.

In another specific embodiment of the invention, the genetically modified microorganism for the production of the desired derivative of 4-hydroxy-2-ketobutyrate is modified for the production of 2,4-dihydroxybutyrate from 4-hydroxy-2-ketobutyrate. This microorganism is particularly described in WO 2014/009435, incorporated herein by reference.

The metabolic pathway for the conversion of 4-hydroxy-2-ketobutyrate into 2,4-dihydroxybutyrate is preferably a one-step pathway.

Preferentially, the method of production according to the present invention is performed with a microorganism, particularly a bacterium, which contains at least one gene encoding an enzyme with 4-hydroxy-2-ketobutyrate reductase activity for the conversion of 4-hydroxy-2-ketobutyrate into 2,4-dihydroxybutyrate. These genes can be exogenous or endogenous, and can be expressed chromosomally or extrachromosomally.

Most preferably the genetically modified microorganism for the production of 2,4-dihydroxybutyrate from 4-hydroxy-2-ketobutyrate used in the method according to the invention expresses at least one of the following genes coding for enzyme having 4-hydroxy-2-ketobutyrate reductase activity well known in the art: genes coding for lactate dehydrogenase such as ldhA from *Oryctalagus cuniculus*, ldhA from *Lactococcus lactis*, lldH from *Geobacillus stearothermophilus*, ldh from *Bacillus subtilis* or ldhA from *Escherichia coli*; genes coding for malate dehydrogenase such as mdh from *Escherichia coli* and genes coding for branched chain 2-hydroxyacid dehydrogenase dehydrogenase such as panE from *Lactococcus lactis*. Functional homologues, functional variants and functional fragments of said genes and proteins are encompassed by the definition.

Preferentially, the genetically modified microorganism of the invention is also modified to stimulate the flux in the oxaloacetate biosynthesis pathway; this result can be achieved by increasing the level of expression of phosphoenolpyruvate carboxylase, encoded by the ppc gene or by increasing the level of expression of pyruvate carboxylase, encoded by the gene pyc. Increasing the expression of phosphoenolpyruvate carboxylase can be accomplished by introducing artificial promoters that drive the expression of the ppc gene, by increasing the number of copies in the cell or by introducing mutations into the ppc gene that increase the activity of the corresponding protein. Increasing the expression of pyruvate carboxylase can be accomplished by introducing a heterologous gene encoding pyruvate carboxylase if the microorganism of the invention is devoid of pyc gene, by introducing strong artificial promoters to drive the expression of the pyc gene, by increasing the number of copies of the gene in the cell or by introducing mutations into the pyc gene that increase the activity of the corresponding protein.

The availability of the intermediate product oxaloacetate can also be increased by attenuating the level of expression of genes coding for phosphoenolpyruvate carboxykinase and/or malic enzymes, encoded by the pckA and/or maeA and/or maeB genes, respectively. This can be done by replacing the wild-type promoter of these genes by a weaker promoter, or by the use of an element destabilizing the corresponding messenger RNA or the protein. If needed, complete attenuation of the genes can also be achieved by the deletion of the corresponding DNA sequences. The invention is also related to the microorganism, particularly a bacterium, used in this particular embodiment of the invention, i.e. a microorganism, particularly a bacterium, presenting an increased availability of the oxaloacetate.

In another embodiment, the genetically modified microorganism is modified to stimulate the flux into the homoserine biosynthesis pathway. This can be achieved by increasing the expression of aspartokinase and homoserine dehydrogenase and/or aspartate semialdehyde dehydrogenase, encoded by the thrA and asd genes, respectively. Increasing the expression of aspartokinase and homoserine dehydrogenase and/or aspartate semialdehyde dehydrogenase can be accomplished by introducing artificial promoters that drive the expression of the thrA and/or asd genes, by increasing the number of copies in the cell or by introducing mutations into the thrA and/or asd genes that increase the activity of the corresponding proteins. The invention is also related to the microorganism, particularly a bacterium, used in this particular embodiment of the invention.

In a particular embodiment, mutations can be introduced into the thrA gene that reduce its sensitivity to the feed-back inhibitor threonine (feed-back desensitized alleles) and thus permit an increased activity in the presence of threonine.

Another way to stimulate the flux into homoserine biosynthesis pathway is to increase the expression of aspartate aminotransferase encoded by aspC gene. Increasing the expression of aspartate aminotransferase can be accomplished by introducing strong artificial promoters that drive the expression of the aspC gene, by increasing the number of copies of the gene in the cell or by introducing mutations into the aspC gene that increase the activity of the corresponding protein.

In a further embodiment of the invention, the genetically modified microorganism is also modified to present an attenuated level of homoserine conversion to other compounds than derivatives of 4-hydroxy-2-ketobutyrate. This result may be achieved by attenuating the level of homoserine consuming enzymes like homoserine kinase and threonine synthase (encoded by thrB and thrC), homoserine O-transsuccinylase (encoded by metA) or dihydrodipicolinate synthase (encoded by dapA). These genes can be attenuated by replacing the natural promoter by a weaker promoter or by elements destabilizing the corresponding messenger RNA or protein. If needed, complete attenuation of the gene can also be achieved by the deletion of the corresponding DNA sequence. The invention is also related to the microorganism, particularly a bacterium, used in this particular embodiment of the invention.

Optionally, the genetically modified microorganism, particularly a bacterium, is further modified to present an attenuated level of 3-hydroxypropionaldehyde conversion to other compounds than 1,3-propanediol. This may be achieved by attenuating the level of 3-hydroxypropionaldehyde consuming enzymes like 3-hydroxypropionaldehyde dehydrogenase (encoded by aldA, aldB). These genes can be attenuated by replacing the natural promoter by a weaker promoter or by elements destabilizing the corresponding messenger RNA or the protein. If needed, complete attenuation of the gene can also be achieved by the deletion of the corresponding DNA sequence. The invention is also related to the microorganism, particularly a bacterium, used in this particular embodiment of the invention.

Also, the genetically modified microorganism may be modified so as the efficiency of the sugar import is increased, either by using a sugar import system not relying on phosphoenolpyruvate (PEP) as phospho donor such as the one encoded by galP that is known to transport glucose, or by providing more phosphoenolpyruvate (PEP) to the sugar-phosphotransferase system. Various means exist that may be used to increase the availability of PEP in a microorganism. In particular, this may be accomplished by attenuating the reaction PEP towards pyruvate. Preferentially, at least one gene selected among pykA and pykF, encoding pyruvate kinase, is attenuated in said strain in order to obtain this result. Another way to increase the availability of PEP is to favour the reaction pyruvate towards PEP. This can be accomplished by increasing the activity of phosphoenolpyruvate synthase which catalyzes the above reaction. This enzyme is encoded by the ppsA gene. Therefore, in the microorganism, the expression of the ppsA gene is preferentially increased. Both modifications can be present in the microorganism simultaneously. Another way to improve the glucose uptake rate of a microorganism is to increase the amount of the PTS permease and to optimize the phosphorylation cascade, by overexpressing at least one of the genes ptsG, ptsH, ptsI and crr or by attenuating the known regulating repression of the PTS system.

In the invention, the genetically modified microorganism may further be modified to use sucrose as a sole source of carbon, as described in WO 2012/004247, incorporated herein by reference.

Particularly the modified microorganism comprises functional genes coding for a PTS sucrose utilization system and/or for a non-PTS sucrose utilization system.

A PTS sucrose utilization system is a system for sucrose utilization based on the transport of sucrose by a phosphoenolpyruvate (PEP)-dependent sucrose phosphotransferase system (Sucrose-PTS). A phosphotransferase system couples the transport of a sugar (e.g. sucrose or glucose) with the phosphorylation of the sugar using PEP as phosphate donor. After transport into the cell, the sucrose-phosphate is cleaved into glucose-6-phosphate and fructose by an invertase. Fructose is then phosphorylated into fructose-6-phosphate by a fructokinase. The genes coding for this PTS sucrose utilization system can be controlled by a regulatory protein.

A non-PTS sucrose utilization system is a system for sucrose utilization based on transport of sucrose by a system independent of phosphoenolpyruvate. After transport into the cell, the sucrose is cleaved into glucose and fructose by an invertase. Fructose is then phosphorylated into fructose-6-phosphate by a fructokinase and glucose is phosphorylated into glucose-6-phosphate by a glucokinase. The genes coding for this non-PTS sucrose utilization system can be controlled by a regulatory protein.

Preferably, the microorganism expresses naturally or has been modified with the introduction of the genes: scrKYABR (scrK coding for a fructokinase, scrY coding for a porin, scrA coding for the Protein IIBC, scrB coding for a sucrose-6-P invertase, scrR coding for a repressor) from *Salmonella*. A conjugative plasmid pUR400 bearing said genes scrKYABR might be used to transform the microorganism. These genes can be used all together in combination, or in any combination comprising at least one of these genes. In particular, the gene scrR can be omitted.

Also preferably, the microorganism expresses naturally or has been modified with the introduction of the genes from *E. coli* EC3132 i.e. the genes cscBKAR coding for a sucrose: proton symport transport system (cscB), a fructokinase (cscK), an invertase (cscA) and a sucrose-specific repressor (cscR). These genes can be used all together in combination or in any combination comprising at least one of these genes. In particular, the gene cscR can be omitted. Homologous genes from other organisms can also be used.

In the method of production of the invention, the microorganism is also genetically modified so as L-homoserine is converted into 4-hydroxy-2-ketobutyrate with a mutant glutamate dehydrogenase converting L-homoserine into 4-hydroxy-2-ketobutyrate by deamination, said mutant glutamate dehydrogenase comprising at least one mutation(s) where amino acid K (Lys) at position 92, by reference to *E. coli* glutamate dehydrogenase of SEQ ID NO: 1, is replaced by a non-polar amino acid.

The gene coding for the mutant glutamate dehydrogenase may be a modified gene endogenous to the said modified microorganism. In the context of the invention the modified gene is mutated to code for a mutant glutamate dehydrogenase converting L-homoserine in 4-hydroxy-2-ketobutyrate by deamination. The mutated protein is identified as an "modified endogenous glutamate dehydrogenase".

In one embodiment, mutations are introduced by directed mutagenesis into the coding sequence of said gene into the genome of said microorganism. The microorganism may be further modified for increasing the expression of the mutated gene. Preferably, the gene coding for a mutant glutamate dehydrogenase is under control of a strong promoter.

The gene coding for the glutamate dehydrogenase may be heterologous to the said modified microorganism of the invention and modified by mutation to code for a mutant glutamate dehydrogenase converting L-homoserine in 4-hydroxy-2-ketobutyrate by deamination. The mutated protein is identified as "heterologous mutated glutamate dehydrogenase".

In one embodiment, the sequence coding for the mutated heterologous glutamate dehydrogenase is introduced into the genome of the microorganism by replacing the coding sequence for the endogenous glutamate dehydrogenase. The microorganism may be further modified for increasing the expression of the mutated gene. Preferably, the gene coding for a mutant glutamate dehydrogenase is under control of a strong promoter.

In another embodiment, the microorganism is modified by introducing one or more copies of the gene coding for a mutant glutamate dehydrogenase converting L-homoserine in 4-hydroxy-2-ketobutyrate by deamination. The microorganism may thus comprises one or more copies of a gene comprising a coding sequence for the endogenous mutated glutamate dehydrogenase under control of regulatory elements for the expression of the gene into the microorganism or one or more copies of a gene comprising a coding sequence for an heterologous mutated glutamate dehydrogenase under control of regulatory elements for the expression of the gene into the microorganism.

Glutamate dehydrogenase (GDH) and genes coding for enzymes having a glutamate dehydrogenase activity are known in the art and are disclosed in Table 1.

TABLE 1

Enzymes having glutamate dehydrogenase activity and genes encoding such glutamate dehydrogenases.

| | PDB acession number | Gene name | Origin |
|---|---|---|---|
| NAD-specific GDH | P39633 | rocG | Bacillus subtilis |
| | Q54VI3 | gluD1 | Dictyostelium discoideum |
| | P94316 | gdhB | Bacteroides fragilis |
| | A0R1C2 | gdh | Mycobacterium smegmatis |
| | Q9HZE0 | gdhB | Pseudomonas aeruginosa |
| | O53203 | gdh | Mycobacterium tuberculosis |
| | P24295 | gdh | Clostridium symbiosum |
| | P00367 | GLUD1 | Homo sapiens |
| | P95544 | gdhA | Prevotella ruminicola |
| | P00365 | gdh-1 | Neurospora crassa |
| NADP-specific GDH | P07262 | GDH1 | Saccharomyces cerevisiae |
| | P00369 | gdh | Neurospora crassa |
| | P78804 | gdh1 | Schizosaccharomyces pombe |
| | P18819 | gdhA | Aspergillus nidulans |
| | P00370 | gdhA | Escherichia coli |
| | P28724 | gdhA | Giardia intestinalis |
| | P54387 | gdhA | Agaricus bisporus |
| | Q9URS1 | GDH | Penicillium chrysogenum |
| | P54388 | GDHA | Laccaria bicolor |

Glutamate dehydrogenase and genes preferred for being mutated to convert L-homoserine into 4-hydroxy-2-ketobutyrate by deamination are selected among rocG from *Bacillus subtilis*, gluD1 from *Dictyostelium discoideum*, gdhB from *Bacteroides fragilis*, gdh from *Mycobacterium smegmatis*, gdhB from *Pseudomonas aeruginosa*, gdh from *Mycobacterium tuberculosis*, gdh from *Clostridium symbiosum*, GLUD1 from *Homo sapiens*, gdhA from *Prevotella ruminicola*, gdh1 from *Neurospora crassa*, GDH1 from *Saccharomyces cerevisiae*, gdh1 from *Schizosaccharomyces pombe*, gdhA from *Aspergillus nidulans*, gdhA from *Escherichia coli*, gdhA from *Giardia intestinalis*, gdhA from *Agaricus bisporus*, GDH from *Penicillium chrysogenum*, GDHA from *Laccaria bicolor*.

Preferably, genes for being mutated to convert L-homoserine into 4-hydroxy-2-ketobutyrate by deamination are gdhA from *E. coli* encoding an anabolic glutamate dehydrogenase and rocG from *B. subtilis* encoding a catabolic glutamate dehydrogenase.

Glutamate dehydrogenases have specific binding sites for glutamate. In a preferred embodiment, the mutant glutamate dehydrogenase comprises at least one mutation(s) into the binding site(s) for glutamate.

The homology modeling of glutamate binding of *E. coli* anabolic glutamate dehydrogenase allowed identifying two residues, K92 and S380 forming a network of hydrogen bonds with the carboxyl group of glutamate side chain (see FIG. 1). This was considered to be a critical factor to discriminate glutamate against other ligands.

Therefore, in the microorganism, the glutamate dehydrogenase comprises at least one mutation where amino acid K (Lys) at position 92, by reference to *E. coli* glutamate dehydrogenase of SEQ ID NO: 1, is replaced with a non polar amino acid, such as A (Ala), F (Phe), G (Gly), I (Ile), L (Leu), M (Met), P (Pro), V (Val) and W (Trp), to prevent hydrogen bonds with the carboxyl group of glutamate. More preferably the amino acid K (Lys) at position 92, by reference to *E. coli* glutamate dehydrogenase of SEQ ID NO: 1, is replaced with an aliphatic non polar amino acid, most preferably with amino acid V (Val).

In another preferred embodiment, the mutant glutamate dehydrogenase comprises a second mutation where amino acid T (Thr) at position 195, by reference to *E. coli* glutamate dehydrogenase of SEQ ID NO: 1, is replaced with amino acid S (Ser).

Amino acids and their position are identified by reference to *E. coli* glutamate dehydrogenase of SEQ ID NO: 1. The person skilled in the art will however be in position to identify the corresponding amino acids responsible for glutamate binding in other glutamate dehydrogenase in using the method used for *E. coli* sequence. Particularly, by simple sequence alignment and without need for a molecular modelling as shown in the examples for *E. coli* sequence, the person skilled in the art can identify homologies and identities in the protein sequences sufficient to identify the corresponding amino acids (see FIG. 2).

In a preferred embodiment, the mutated glutamate dehydrogenase has the sequence as depicted in SEQ ID NO: 2 or in SEQ ID NO: 3.

The homology modeling of glutamate binding of *B. subtilis* catabolic glutamate dehydrogenase allowed identifying two residues, K80 and S358 forming a network of hydrogen bonds with the carboxyl group of glutamate side chain. This was considered to be a critical factor to discriminate glutamate against other ligands.

Therefore, in a preferred embodiment, the glutamate dehydrogenase comprises at least one mutation where amino acid K (Lys) at position 80, by reference to *B. subtilis* glutamate dehydrogenase of SEQ ID NO: 4, is replaced with a non polar amino acid, such as A (Ala), F (Phe), G (Gly), I (Ile), L (Leu), M (Met), P (Pro), V (Val) and W (Trp), to prevent hydrogen bonds with the carboxyl group of glutamate. More preferably the amino acid K (Lys) at position 80, by reference to *B. subtilis* glutamate dehydrogenase of SEQ ID NO: 4, is replaced with an aliphatic non polar amino acid, most preferably amino acid V (Val).

In another preferred embodiment, the mutant glutamate dehydrogenase comprises a second mutation where amino acid T (Thr) at position 184, by reference to *B. subtilis* glutamate dehydrogenase of SEQ ID NO: 4, is replaced with amino acid S (Ser).

Amino acids and their position are identified by reference to *B. subtilis* glutamate dehydrogenase of SEQ ID NO: 4. The person skilled in the art will however be in position to identify the corresponding amino acids responsible for glutamate binding in other glutamate dehydrogenase in using the method used for *B. subtilis* sequence. Particularly, by simple sequence alignment and without need for a molecular modelling as shown in the examples for *B. subtilis* sequence, the person skilled in the art can identify homologies and identities in the protein sequences sufficient to identify the corresponding amino acids.

In a preferred embodiment, the mutated glutamate dehydrogenase has the sequence as depicted in SEQ ID NO: 5 or in SEQ ID NO: 6.

In a preferred embodiment, the method for the production of derivatives of 4-hydroxy-2-ketobutyrate chosen among 1,3-propanediol or 2,4-dihydroxybutyrate by fermentation according to the present invention is comprising culturing the microorganism genetically modified for the production of the desired derivative of 4-hydroxy-2-ketobutyrate as described above in a culture medium comprising a source of carbon and recovering the desired derivative of 4-hydroxy-2-ketobutyrate from the culture medium, wherein the modified microorganism is a microorganism further comprising a gene coding for a mutant glutamate dehydrogenase converting L-homoserine into 4-hydroxy-2-ketobutyrate by deamination as defined above, and preferable as defined in the examples.

Methods for the production of the desired derivative of 4-hydroxy-2-ketobutyrate by fermentation of modified microorganisms and recovery of the desired derivative of 4-hydroxy-2-ketobutyrate from the fermentation medium are known in the art, including WO 2010/076324, WO 2012/004247 and WO 2014/009435, incorporated herein by reference.

Fermentation mediums and sources of carbon are also well known. According to the invention, the terms "fermentative process', 'fermentation" or 'culture' are used interchangeably to denote the growth of microorganism. This growth is generally conducted in fermenters with an appropriate growth medium adapted to the microorganism being used.

A "culture medium" designates a medium (e.g., a sterile, liquid media) comprising nutrients essential or beneficial to the maintenance and/or growth of the cell such as carbon sources or carbon substrates or carbohydrate, nitrogen sources, for example, peptone, yeast extracts, meat extracts, malt extracts, urea, ammonium sulfate, ammonium chloride, ammonium nitrate and ammonium phosphate; phosphorus sources, for example, monopotassium phosphate or dipotassium phosphate; trace elements (e.g., metal salts), for example magnesium salts, cobalt salts and/or manganese salts; as well as growth factors such as amino acids and vitamins.

The term "source of carbon", "carbon source" or "carbon substrate" according to the present invention refers to any carbon source capable of being metabolized by a microorganism wherein the substrate contains at least one carbon atom.

The term "carbohydrate" refers to any carbon source capable of being metabolized by a microorganism and containing at least one carbon atom, two atoms of hydrogen and one atom of oxygen.

The carbohydrate is selected among the group consisting of monosaccharides such as glucose, fructose, mannose, xylose, arabinose, galactose and the like, disaccharides such as sucrose, cellobiose, maltose, lactose and the like, oligosaccharides such as raffinose, stacchyose, maltodextrins and the like, polysaccharides such as cellulose, hemicellulose, starch and the like, methanol, formaldehyde and glycerol. Especially preferred carbon sources are arabinose, fructose, galactose, glucose, lactose, maltose, sucrose, xylose or a mixture thereof. More preferably carbon source is sucrose.

In a particular embodiment of the invention, the carbon source is derived from renewable feed-stock. Renewable feed-stock is defined as raw material required for certain industrial processes that can be regenerated within a brief delay and in sufficient amount to permit its transformation into the desired product. Vegetal biomass treated or not, is an interesting renewable carbon source.

Those skilled in the art are able to define the culture conditions for the microorganisms according to the invention. In particular the bacteria are fermented at a temperature between 20° C. and 55° C., preferentially between 25° C. and 40° C., and more specifically about 30° C. to 37° C. for *E. coli*.

This process can be carried out either in a batch process, in a fed-batch process or in a continuous process. It can be carried out under aerobic, micro-aerobic or anaerobic conditions.

'Under aerobic conditions' means that oxygen is provided to the culture by dissolving the gas into the liquid phase. This could be obtained by (1) sparging oxygen containing gas (e.g. air) into the liquid phase or (2) shaking the vessel containing the culture medium in order to transfer the oxygen contained in the head space into the liquid phase. The main advantage of the fermentation under aerobic conditions is that the presence of oxygen as an electron acceptor improves the capacity of the strain to produce more energy under the form of ATP for cellular processes. Therefore the strain has its general metabolism improved.

Micro-aerobic conditions are defined as culture conditions wherein low percentages of oxygen (e.g. using a mixture of gas containing between 0.1 and 10% of oxygen, completed to 100% with nitrogen), is dissolved into the liquid phase.

Anaerobic conditions are defined as culture conditions wherein no oxygen is provided to the culture medium. Strictly anaerobic conditions are obtained by sparging an inert gas like nitrogen into the culture medium to remove traces of other gas. Nitrate can be used as an electron acceptor to improve ATP production by the strain and improve its metabolism.

The action of "recovering the desired derivative of 4-hydroxy-2-ketobutyrate from the culture medium" designates the action of collecting the produced desired derivative of 4-hydroxy-2-ketobutyrate from the fermentation medium whatever its purity degree. "Recovering" means collecting the first product directly obtained from the fermentative process (fermentation must) which contains the product of interest (in this case desired derivative of 4-hydroxy-2-ketobutyrate) and other co-products of the fermentation so with a more or less acceptable purity degree.

The above method can also comprise a further step of purifying the desired derivative of 4-hydroxy-2-ketobutyrate if the purity degree obtained after the step of recovering is less acceptable. The "purifying" step consists of specifically purify the product of interest (in this case desired derivative of 4-hydroxy-2-ketobutyrate) in order to obtain said product of interest with an improved purity degree that is to say by eliminating all the co-products.

For example 1,3-propanediol might be recovered and purified by techniques and means well known by the man skilled in the art and have notably been described in patent applications, WO 2009/068110 and WO 2010/037843 herein incorporated by reference.

Another object of the present invention is also the genetically modified microorganism used for the production of derivatives of 4-hydroxy-2-ketobutyrate chosen among 1,3-propanediol and 2,4-dihydroxybutyrate as described above. All preferred embodiments disclosed herein for the microorganism to be used in the method of production of the invention as disclosed above apply mutatis mutandis to the genetically modified microorganism as such.

In one other object, the present invention relates to the use of a genetically modified microorganism comprising a gene coding for a mutant glutamate dehydrogenase converting by deamination L-homoserine into 4-hydroxy-2-ketobutyrate and wherein said mutant glutamate dehydrogenase comprises at least one mutation where amino acid K (Lys) at position 92, by reference to *E. coli* glutamate dehydrogenase of SEQ ID NO: 1, is replaced by a non polar amino acid, for improving the production a derivatives of 4-hydroxy-2-ketobutyrate chosen among 1,3-propanediol and 2,4-dihydroxybutyrate. The genetically modified microorganism comprising said mutant glutamate dehydrogenase to be used for the production of said derivatives of 4-hydroxy-2-ketobutyrate may be already modified for the production of the desired derivative of 4-hydroxy-2-ketobutyrate.

EXAMPLES

Abbreviations 1, 3-propanediol (PDO); polytrimethylene terephthalate (PTT); S-adenosyl methionine (SAM); glutamate dehydrogenase (GDH); isopropyl β-D-thiogalactopyranoside (IPTG); thiamin diphophate (ThDP); pyruvate decarboxylase (PDC); alcohol dehydrogenase (YQHD); Thiamin (VB1); pentose phosphate pathway (PPP); phosphotransferase system (PTS); glyceraldehyde 3-phosphate dehydrogenase (GAPDH); branched-chain alpha-keto acid decarboxylase (KDC).

Materials and Methods

1 Molecular Modeling

Homology models of *E. coli* glutamate dehydrogenase (GDH) with glutamate were generated based on the structure of *Clostridium symbiosum* glutamate dehydrogenase (Protein Data Bank code 1BGV) using the molecular modeling software Modeller (Sali et al., 1993). The molecular docking software Autodock (Morris et al., 1998) was used to refine the conformations of the mutated residues and the ligand.

2 Bacterial Strains and Plasmids Construction

*E. coli* JM109 was routinely used for the construction of plasmids and *E. coli* BL21 (DE3) cells (New England Biolabs) was used as the host for enzyme overexpression and purification. Primers used are listed below.

```
gdh_F
                                              (SEQ ID NO: 7)
5'-cagccatatggatcagacatattctctggagtcattcc-3' gdh_R
                                              (SEQ ID NO: 8)
5'-atatgtcgacttaaatcacaccctgcgccag-3' pdc_F
                                              (SEQ ID NO: 9)
5'-cagccatatgagttatactgtcggtacct-3' pdc_R
                                             (SEQ ID NO: 10)
5'-attaaagcttctagtggtggtggtggtggtggaggagcttgttaaca
ggctta-3' kdc_F
                                             (SEQ ID NO: 11)
5'-cagccatatgtataccgtgggtgattatctg-3' kdc_R
                                             (SEQ ID NO: 12)
5'-attaaagcttctagtggtggtggtggtggtgtttgttctgctcggca
aaca-3' yqhD_F
                                             (SEQ ID NO: 13)
5'-attaaagcttaactttaagaaggagatatacagatgaacaactttaa
tctgcacac-3' yqhD_R
                                             (SEQ ID NO: 14)
5'-attactcgaggcggcggcttcgtatatac-3'
```

The gdhA gene encoding the wildtype glutamate dehydrogenase (GDH) was amplified by PCR from genomic DNA of *E. coli* MG1655, double-digested with NdeI and SalI and cloned into plasmid pET-28a (+) (Novagen), designated as pET-gdhA. The pdc gene encoding the wildtype pyruvate decarboxylase (PDC) was amplified by PCR from genomic DNA of *Zymomonas mobilis* DSM 3580, double-digested with NdeI and HindIII and cloned into plasmid pET-28a (+), designated as pET-pdc. The yqhD gene encoding the wildtype alcohol dehydrogenase (YqhD) was amplified by PCR from genomic DNA of *E. coli* MG1655, double-digested with HindIII and XhoI and cloned into plasmid pET-28a (+), designated as pET-yqhD.

Point mutations were introduced by using QuikChange® site-directed mutagenesis kits (Strategene) according to the standard protocol. Primers used for mutations are listed below.

```
K92Q
                                             (SEQ ID NO: 15)
5'-ccatcggcccgtaccagggcggtatgcgctt-3'

K92Q_antisense
                                             (SEQ ID NO: 16)
5'-aagcgcataccgccctggtacgggccgatgg-3'

S380Q
                                             (SEQ ID NO: 17)
5'-tgctggtggcgtcgctacacagggcctggaa-3'

S380Q_antisense
                                             (SEQ ID NO: 18)
5'-ttccaggccctgtgtagcgacgccaccagca-3'

T195S
                                             (SEQ ID NO: 19)
5'-ccgcctgcgtcttcagcggtaagggc-3'

T195S_antisense
                                             (SEQ ID NO: 20)
5'-gcccttaccgctgaagacgcaggcgg-3'

K92V
                                             (SEQ ID NO: 21)
5'-ccatcggcccgtacgtaggcggtatgcgct-3'

K92V_antisense
                                             (SEQ ID NO: 22)
5'-agcgcataccgcctacgtacgggccgatgg-3'

T195Q
                                             (SEQ ID NO: 23)
5'-caataccgcctgcgtcttccagggtaagggccttcatttg-3'

T195Q_antisense
                                             (SEQ ID NO: 24)
5'-caaatgaaaggcccttaccctggaagacgcaggcggtattg-3'

K92M
                                             (SEQ ID NO: 25)
5'-ctgccatcggcccgtacatgggcggtatgcg-3'

K92M_antisense
                                             (SEQ ID NO: 26)
5'-cgcataccgcccatgtacgggccgatggcag-3'

S380N
                                             (SEQ ID NO: 27)
5'-ctaatgctggtggcgtcgctacaaatggcctggaaatgg-3'

S380N_antisense
                                             (SEQ ID NO: 28)
5'-ccatttccaggccatttgtagcgacgccaccagcattag-3'

V377L_S380N
                                             (SEQ ID NO: 29)
5'-ggctaatgctggtggcctcgctacaaatggcctggaaatggcac-3'

V377L_S380N_antisense
                                             (SEQ ID NO: 30)
5'-gtgccatttccaggccatttgtagcgaggccaccagcattagcc-3'
```

-continued

T195V (SEQ ID NO: 31)
5'-accgcctgcgtcttcgtcggtaagggcctttc-3'

T195V_antisense (SEQ ID NO: 32)
5'-gaaaggcccttaccgacgaagacgcaggcggt-3'

3 Protein Expression and Purification Enzymes were expressed in *E. coli* BL21(DE3) cells (New England Biolabs) using pET derived plasmids. The recombinant cells were first grown in LB media supplemented with 50 µg/ml Kanamycin at 37° C. until the $OD_{600}$ reached 0.6 and gene expression was induced by adding 0.1 mM isopropyl β-D-thiogalactopyranoside (IPTG) for an additional 6 h. The harvested cells were washed twice with 20 mM Tris-HCl buffer (pH 7.0) and suspended in a buffer of 50 mM $Na_2HPO_4$ (pH 7.0), 0.2 mM EDTA and 0.1 mM dithiothreitol. Suspended cells were disrupted by sonication and centrifuged at 100,000×g for 1 h. The supernatant was purified using a $Ni^{2+}$-NTA column (GE Healthcare Bio-Sciences, Piscataway, N.J.) to obtain samples for activity assay. The purity of enzymes was checked by SDS-PAGE and the protein concentrations were quantified using a Bio-Rad protein assay kit (Bio-Rad Laboratories).

4 Enzyme Assay and In Vitro PDO Production

The enzyme activity of GDH was determined at 25° C. by monitoring the absorbance change of NADPH at 340 nm using a Multiskan spectrophometer (Thermo Scientific, Germany). Initial rate measurements were carried out in the reaction mixture of 100 mM homoserine, 1 mM NADP, 50 mM potassium phosphate (pH 7.0) and appropriate amount of enzyme (Wang et al., 2001). Kinetic constants were obtained from non-linear regression data analysis and expressed as the mean±S.D.

The in vitro production of 1, 3-propanediol was carried out at 37° C. in 2 mL of reaction mixture of 100 mM homoserine, 2 mM NADP, 50 mM potassium diphosphate (pH 7.0), 5 mM $MgSO_4$, 1.5 mM thiamin diphophate (ThDP) and appropriate amount of enzymes (molecular ratio of GDH:PDC:YqhD at about 10:10:1). Samples were taken in 24 hours and measured by GC-MS. Wildtype GDH was used as reference for comparison.

5 Construction of a Combined Module for In Vivo Production of 1, 3-Propendiol from Homoserine The plasmid pZA-pdc-yqhD used for in vivo experiment was constructed with In Fusion kit (Clotech). The pdc gene was amplified from pET-pdc with the primers pdc_F and pdc_R. yqhD was amplified from pET-yqhD with the primers yqhD_F2 and yqhD_R2. The plasmid back bone was amplified by PCR with the primers pZA_F and pZA_R.

The plasmid pZA-pdc-yqhD was single-digested with KpnI and ligated with wildtype gdhA gene or its mutant (K92V/T195S) with In Fusion Kit. The products are designated as pZA-gdhA-pdc-yqhD or pZA-gdhA-K92V/T195S-pdc-yqhD, respectively. The wildtype gdhA gene and K92V/T195S mutant were amplified by PCR from plasmids constructed in this study using the primers gdh_F2 and gdh_R2. Plasmids pZA-gdhA-pdc-yqhD and pZA-gdhA-K92V/T195S-pdc-yqhD were transformed into *E. coli* MG1655ΔThrB, respectively. The resulting strains are designated as wildtype and mutant strain. The homoserine kinase gene thrB was knocked out from wild type *E. coli* MG1655 by Red combination. Primers used are listed below.

kdcA_F (SEQ ID NO: 33)
5'-gaggagaaaggtaccaactttaagaaggagatatacatatgtataccgtgg-3' kdcA_R (SEQ ID NO: 34)
5'-ttatttgttctgctcggcaaacagtttacccattttttcag-3' yqhD_F2

(SEQ ID NO: 35)
5'-gagcagaacaaataaaactttaagaaggagatatacatatgaacaactttaatctgcacac-3' yqhD_R2

(SEQ ID NO: 36)
5'-atgcctctagagtcattagcgggcggcttcgtata-3' pZA_F (SEQ ID NO: 37)
5'-tgactctagaggcatcaaataaaacgaaagg-3' pZA_R (SEQ ID NO: 38)
5'-ggtacctttctcctctttaatgaattcggtc-3' gdh_F2

(SEQ ID NO: 39)
5'-ttaaagaggagaaagacatatggatcagacatattctctggagtca-3' gdh_R2

(SEQ ID NO: 40)
5'-tccttcttaaagttgttaaatcacaccctgcgccagc-3'

We also constructed a reference strain as described in patent applications EP 2 540 834 and WO 2013/052717 which utilize the phosphoserine aminotransferase (SerC), branched-chain alpha-ketoacid decarboxylase (KdcA) and alcohol dehydrogenase (YqhD) to catalyze the transformation of homoserine to PDO. The recombinant plasmid pZA-serC-kdcA-yqhD was constructed as mentioned above by the insertion of serC gene encoding the phosphoserine aminotransferase of *E. coli*, the kdcA gene encoding the branched-chain alpha-ketoacid decarboxylase of *Lactococcus lactis* and yqhD gene of *E. coli*.

6 Cultivation

Strain cultivations were performed in shake flasks. *E. coli* MG1655ΔThrB (pZA-gdhA-pdc-yqhD), *E. coli* MG1655ΔThrB (pZA-gdhA K92V/T195S-pdc-yqhD), and *E. coli* MG1655ΔThrB (pZA-serC-kdcA-yqhD) were initially grown in 50 mL corning tubes containing 10 mL of LB medium for 12 h. The seed cultures were then inoculated into 500 mL conical flasks containing 30 mL culture medium with a start OD600 of 0.1. The culture medium contained (g/L) 20 Glucose, 1 $KH_2PO_4$, 1 $MgSO_4$, 2 Yeast extract, 0.01 $FeSO_4.7H_2O$, 0.01 $MnSO_4.7H_2O$, 1 Threonine, 0.01 Thiamin (VB1) and 30 $CaCO_3$. A 5 g/L homoserine was added for proof of the concept. The cultivation was maintained at 32° C. and 250 rpm. Glucose was measured with YSI; the concentration of PDO was measured with GC-MS.

Results

Engineering Glutamate Dehydrogenase to Utilize Homoserine as Substrate

In general, amino acid dehydrogenase (E.C. 1.4.1-) can catalyze the deamination of amino acids. Considering the structural similarity of substrates, glutamate dehydrogenase (GDH) was selected as the first candidate for engineering the deamination of homoserine.

The homology modeling of glutamate binding of *E. coli* GDH is shown in FIG. 1. Two residues, K92 and S380 form a network of hydrogen bonds with the carboxyl group of glutamate side chain. This is considered to be a critical factor to discriminate glutamate against other ligands. Other residues located within the binding sites of glutamate, especially T195, V377, S380 and A166 were also taken into account. All these residues were subjected to in silico mutagenesis and docking screening and 16 combinatorial mutations (K92Q, S380Q, K92V, T195S, K92M, V377L/S380N, T195V, A166S, K92Q/S380Q, K92Q/T195S, T195S/S380Q, K92V/T195S, K92V/T195Q, K92V/S380Q, K92M/S380N, K92M/T195V/V377L/S380N) are chosen for experimental characterization.

The wildtype GDH showed a very low activity towards homoserine. Two of the designed mutants, K92V, K92V/T195S showed higher activities using homoserine as substrate. The specific activities of mutants K92V/T195S towards homoserine was 340 mU/mg protein while the specific activity towards glutamate were 114 mU/mg, respectively. The results provided an initial proof-of-concept that homoserine can be efficiently deaminated to 4-hydroxy-2-ketobutyrate by the mutated GDH.

Kinetic parameters of the wildtype and mutated GDHs were obtained in vitro. The mutation of only K92 improved the Vmax for homoserine. GDH with mutations of both K92 and T195 showed a higher Vmax for both homoserine and NADP compared to the wild type.

Examination of In Vitro 1, 3-Propanediol Production

To catalyze the decarboxylation of 4-hydroxy-2-ketobutyrate to 3-hydroxypropionaldehyde, two candidates were selected: pyruvate decarboxylase (PDC) from *Zymomonas mobilis* DSM 3580 and branched-chain alpha-keto acid decarboxylase (KDC) from *Lactococcus lactis*.

Since 4-hydroxy-2-ketobutyrate, the substrate for the designed reaction, is not commercially available, a coupled reaction was designed to directly test the in vitro production of PDO. As described in Materials and Methods, the in vitro system used defined amounts of three purified enzymes to catalyze the transformation of homoserine to PDO: wildtype or mutated GDH, PDC or KDC, and YqhD. All of the designed mutants could catalyze the transformation of homoserine to 4-hydroxy-2-ketobutyrate. The combination of GDH K92V/T195S, PDC from *Zymomonas mobilis* and YqhD produced the highest PDO in the reaction (35 mg/L), while reaction with wildtype GDH or with KDC under the same conditions didn't give detectable PDO.

Test of the Combined Pathway for In Vivo Production of 1, 3-Propanediol from Homoserine and Glucose In its native form, *E. coli* is unable to produce PDO. To test the new pathway, three key genes (gdhA or gdhA K92V/T195S, pdc and yqhD) were integrated into a plasmid pZA-gdhA-K92V/T195S-pdc-yqhD and overexpressed in the strain *E. coli* MG1655 ΔThrB. The resulting strains also did not produce detectable PDO by using glucose as sole carbon source. We speculate that this was due to the limitation of precursor supply. The synthesis of homoserine in *E. coli* is subjected to complex regulation, for example, the key enzymes aspartokinase and homoserine dehydrogenase are feedback inhibited by different amino acids. Thus, homoserine was added into the medium to enhance the precursor supply. Homoserine appeared to be toxic and reduced the cell growth and glucose consumption. Over expression of mutated GDH K92V/T195S led to a faster PDO accumulation. In shaking flask cultures, *E. coli* MG1655ΔThrB (pZA-gdhA-K92V/T195S-pdc-yqhD) produced 51.5±4.9 mg/L PDO at the end of cultivation which was 110% higher than that of the MG1655ΔThrB (pZA-gdhA-pdc-yqhD) control, indicating that the reengineered gdhA significantly improved the PDO synthesis pathway. The cell growth and PDO production of *E. coli* MG1655ΔThrB (pZA-gdhA-K92V/T195S-pdc-yqhD) was also much higher than those of the reference strain which utilize the phosphoserine aminotransferase (SerC), branched-chain alpha-ketoacid decarboxylase (KdcA) and alcohol dehydrogenase (YqhD) to catalyze the transformation of homoserine to PDO.

Production of 2,4-dihydroxybutyrate

Optimized strains for 2,4-dihydroxybutyrate production described in patent application WO2014/009435 as strains ECE73, ECE74, ECE75 and ECE76 have been constructed and named respectively MTX1, MTX2, MTX3 and MTX4. Strains MTX3 and MTX4 were further modified in order to overexpress our glutamate dehydrogenase mutants disclosed in SEQ ID: 2, SEQ ID: 3 and SEQ ID: 5, giving rise to strains MTX5, MTX6 and MTX7 corresponding to modifications introduced into MTX3 and to strains MTX8, MTX9 and MTX10 corresponding to modifications introduced into MTX4. More precisely, genes encoding the GdhA mutant or RocG mutant proteins were cloned onto the pEXT20-DHB (described in patent application WO2014/009435) in lieu of ilvE gene from *E. coli* encoding the homoserine transaminase and introduced into the recipient strains.

2,4-DHB production of strains MTX5, MTX6 and MTX7 was compared to strain MTX3 whereas 2,4-DHB production of strains MTX8, MTX9 and MTX10 were compared to strain MTX4. After 24 h cultivation, the DHB concentration in the supernatant of the different strains was quantified by LC-MS analyses. The strains overproducing the mutants of glutamate dehydrogenase produced at least 10% more 2,4-dihydroxybutyrate than reference strains MTX3 and MTX4.

REFERENCES

Carrier T & Keasling J., (1999), *Biotechnol Prog.*, 15 (1): 58-64
Morris, G. M., Goodsell, D. S., Halliday, R. S., Huey, R., (1998), *J. Comput. Chem.*, 19: 1639-1662
Sali, A. and Blundell, T. L., (1993), *J. Mol. Biol.*, 234: 779-815
Salis H., (2011), *Methods Enzymol.*, 498:19-42
Segel I., (1993), Enzyme kinetics, John Wiley & Sons, pp. 44-54 and 100-112
Wang, X. G., Britton, K. L., Stillman, T. J., Rice, D. W., (2001), *Eur. J. Biochem.*, 268: 5791-5799

The invention claimed is:

1. A method for the production of derivatives of 4-hydroxy-2-ketobutyrate selected in the group consisting of 1,3-propanediol and 2,4-dihydroxybutyrate by culturing a genetically modified microorganism for the production of the desired derivative of 4-hydroxy-2-ketobutyrate, wherein the genetically modified microorganism further comprises a gene coding for a mutant glutamate dehydrogenase converting by deamination L-homoserine into 4-hydroxy-2-ketobutyrate and wherein said mutant glutamate dehydrogenase comprises at least one mutation where amino acid K (Lys) at position 92, by reference to *E. coli* glutamate dehydrogenase of SEQ ID NO: 1, is replaced with amino acid V (Val).

2. The method of claim 1, wherein the mutant glutamate dehydrogenase comprises a second mutation where amino acid T (Thr) at position 195, by reference to *E. coli* glutamate dehydrogenase of SEQ ID NO: 1, is replaced with amino acid S (Ser).

3. The method of claim 1, wherein the gene coding for the mutant glutamate dehydrogenase is a modified gene endogenous to the said modified microorganism.

4. The method of claim 1, wherein the gene coding for the mutant glutamate dehydrogenase is a modified gene heterologous to the said modified microorganism.

5. The method of claim 1, wherein the gene coding for a mutant glutamate dehydrogenase is under control of a strong promoter.

6. The method of claim 1, wherein the genetically modified microorganism comprises one or more copies of the gene coding for a mutant glutamate dehydrogenase converting L-homoserine into 4-hydroxy-2-ketobutyrate by deamination.

7. The method of claim 1, wherein the genetically modified microorganism is selected in the group consisting of Enterobacteriaceae, Clostridiaceae, Bacillaceae, Streptomycetaceae and Corynebacteriaceae.

8. The method of claim 1, wherein the genetically modified microorganism for the production of the desired derivative of 4-hydroxy-2-ketobutyrate is a genetically modified microorganism for the production of 1,3-propanediol from 4-hydroxy-2-ketobutyrate in a two-steps pathway by expressing:
(i) at least one gene encoding an enzyme having a 2-keto acid decarboxylase activity for the conversion of 4-hydroxy-2-ketobutyrate into 3-hydroxypropionaldehyde, and
(ii) at least one gene encoding an enzyme having hydroxy aldehyde reductase activity for the conversion of 3-hydroxypropionaldehyde into 1,3-propanediol.

9. The method of claim 8 wherein the genetically modified microorganism for the production of 1,3-propanediol from 4-hydroxy-2-ketobutyrate expresses:
(i) at least one gene encoding an enzyme having a 2-keto acid decarboxylase activity for the conversion of 4-hydroxy-2-ketobutyrate into 3-hydroxypropionaldehyde selected in the group consisting of kivD gene from *Lactococcus lactis* and pdc gene from *Zymomonas mobilis*, and
(ii) at least yqhD gene from *Escherichia coli* encoding an enzyme having hydroxy aldehyde reductase activity for the conversion of 3-hydroxypropionaldehyde into 1,3-propanediol.

10. The method of claim 1, wherein the genetically modified microorganism for the production of the desired derivative of 4-hydroxy-2-ketobutyrate is a genetically modified microorganism for the production of 2,4-dihydroxybutyrate from 4-hydroxy-2-ketobutyrate in a one-step pathway by expressing at least one gene encoding an enzyme having 4-hydroxy-2-ketobutyrate reductase activity for the conversion of 4-hydroxy-2-ketobutyrate into 2,4-dihydroxybutyrate.

11. The method of claim 10, wherein the genetically modified microorganism for the production of 2,4-dihydroxybutyrate from 4-hydroxy-2-ketobutyrate expresses at least one gene selected in the group consisting of ldhA from *Oryctalagus cuniculus*, ldhA from *Lactococcus lactis*, lldH from *Geobacillus stearothermophilus*, ldh from *Bacillus subtilis*, ldhA from *Escherichia coli*, mdh from *Escherichia coli* and panE from *Lactococcus lactis*.

12. The method of claim 1 comprising:
culturing in a culture medium comprising a source of carbon said genetically modified microorganism for the production of derivatives of 4-hydroxy-2-ketobutyrate selected in the group consisting of 1,3-propanediol and 2,4-dihydroxybutyrate and comprising a gene coding for said mutant glutamate dehydrogenase converting by deamination L-homoserine into 4-hydroxy-2-ketobutyrate and
recovering the desired derivative of 4-hydroxy-2-ketobutyrate from the culture medium.

13. A genetically modified microorganism as defined in the method for the production of derivatives of 4-hydroxy-2-ketobutyrate selected in the group consisting of 1,3-propanediol and 2,4-dihydroxybutyrate according to claim 1.

14. The genetically modified microorganism of claim 13 wherein it is selected in the group consisting of Enterobacteriaceae, Clostridiaceae, Bacillaceae, Streptomycetaceae and Corynebacteriaceae.

15. The method of claim 8, wherein the mutant glutamate dehydrogenase comprises a second mutation where amino acid T (Thr) at position 195, by reference to *E. coli* glutamate dehydrogenase of SEQ ID NO: 1, is replaced with amino acid S (Ser).

16. The method of claim 10, wherein the mutant glutamate dehydrogenase comprises a second mutation where amino acid T (Thr) at position 195, by reference to *E. coli* glutamate dehydrogenase of SEQ ID NO: 1, is replaced with amino acid S (Ser).

17. A genetically modified microorganism as defined in the method for the production of derivatives of 4-hydroxy-2-ketobutyrate according to claim 2.

* * * * *

SEQUENCE LISTING

<160> NUMBER OF SEQ ID NOS: 40

<210> SEQ ID NO 1
<211> LENGTH: 447
<212> TYPE: PRT
<213> ORGANISM: Escherichia coli

<400> SEQUENCE: 1

```
Met Asp Gln Thr Tyr Ser Leu Glu Ser Phe Leu Asn His Val Gln Lys
1               5                   10                  15

Arg Asp Pro Asn Gln Thr Glu Phe Ala Gln Ala Val Arg Glu Val Met
            20                  25                  30

Thr Thr Leu Trp Pro Phe Leu Glu Gln Asn Pro Lys Tyr Arg Gln Met
        35                  40                  45

Ser Leu Leu Glu Arg Leu Val Glu Pro Glu Arg Val Ile Gln Phe Arg
    50                  55                  60

Val Val Trp Val Asp Asp Arg Asn Gln Ile Gln Val Asn Arg Ala Trp
65                  70                  75                  80

Arg Val Gln Phe Ser Ser Ala Ile Gly Pro Tyr Lys Gly Gly Met Arg
                85                  90                  95

Phe His Pro Ser Val Asn Leu Ser Ile Leu Lys Phe Leu Gly Phe Glu
            100                 105                 110

Gln Thr Phe Lys Asn Ala Leu Thr Thr Leu Pro Met Gly Gly Gly Lys
        115                 120                 125

Gly Gly Ser Asp Phe Asp Pro Lys Gly Lys Ser Glu Gly Glu Val Met
    130                 135                 140

Arg Phe Cys Gln Ala Leu Met Thr Glu Leu Tyr Arg His Leu Gly Ala
145                 150                 155                 160

Asp Thr Asp Val Pro Ala Gly Asp Ile Gly Val Gly Gly Arg Glu Val
                165                 170                 175

Gly Phe Met Ala Gly Met Met Lys Lys Leu Ser Asn Asn Thr Ala Cys
            180                 185                 190

Val Phe Thr Gly Lys Gly Leu Ser Phe Gly Gly Ser Leu Ile Arg Pro
        195                 200                 205

Glu Ala Thr Gly Tyr Gly Leu Val Tyr Phe Thr Glu Ala Met Leu Lys
    210                 215                 220

Arg His Gly Met Gly Phe Glu Gly Met Arg Val Ser Val Ser Gly Ser
225                 230                 235                 240

Gly Asn Val Ala Gln Tyr Ala Ile Glu Lys Ala Met Glu Phe Gly Ala
                245                 250                 255

Arg Val Ile Thr Ala Ser Asp Ser Gly Thr Val Val Asp Glu Ser
            260                 265                 270

Gly Phe Thr Lys Glu Lys Leu Ala Arg Leu Ile Glu Ile Lys Ala Ser
        275                 280                 285

Arg Asp Gly Arg Val Ala Asp Tyr Ala Lys Glu Phe Gly Leu Val Tyr
    290                 295                 300

Leu Glu Gly Gln Gln Pro Trp Ser Leu Pro Val Asp Ile Ala Leu Pro
305                 310                 315                 320

Cys Ala Thr Gln Asn Glu Leu Asp Val Asp Ala Ala His Gln Leu Ile
                325                 330                 335

Ala Asn Gly Val Lys Ala Val Ala Glu Gly Ala Asn Met Pro Thr Thr
            340                 345                 350

Ile Glu Ala Thr Glu Leu Phe Gln Gln Ala Gly Val Leu Phe Ala Pro
        355                 360                 365

Gly Lys Ala Ala Asn Ala Gly Gly Val Ala Thr Ser Gly Leu Glu Met
    370                 375                 380

Ala Gln Asn Ala Ala Arg Leu Gly Trp Lys Ala Glu Lys Val Asp Ala
385                 390                 395                 400

Arg Leu His His Ile Met Leu Asp Ile His His Ala Cys Val Glu His
                405                 410                 415
```

```
Gly Gly Glu Gly Glu Gln Thr Asn Tyr Val Gln Gly Ala Asn Ile Ala
            420                 425                 430

Gly Phe Val Lys Val Ala Asp Ala Met Leu Ala Gln Gly Val Ile
        435                 440                 445

<210> SEQ ID NO 2
<211> LENGTH: 447
<212> TYPE: PRT
<213> ORGANISM: Escherichia coli

<400> SEQUENCE: 2

Met Asp Gln Thr Tyr Ser Leu Glu Ser Phe Leu Asn His Val Gln Lys
1               5                   10                  15

Arg Asp Pro Asn Gln Thr Glu Phe Ala Gln Ala Val Arg Glu Val Met
                20                  25                  30

Thr Thr Leu Trp Pro Phe Leu Glu Gln Asn Pro Lys Tyr Arg Gln Met
            35                  40                  45

Ser Leu Leu Glu Arg Leu Val Glu Pro Glu Arg Val Ile Gln Phe Arg
    50                  55                  60

Val Val Trp Val Asp Asp Arg Asn Gln Ile Gln Val Asn Arg Ala Trp
65                  70                  75                  80

Arg Val Gln Phe Ser Ser Ala Ile Gly Pro Tyr Val Gly Gly Met Arg
                85                  90                  95

Phe His Pro Ser Val Asn Leu Ser Ile Leu Lys Phe Leu Gly Phe Glu
            100                 105                 110

Gln Thr Phe Lys Asn Ala Leu Thr Thr Leu Pro Met Gly Gly Gly Lys
        115                 120                 125

Gly Gly Ser Asp Phe Asp Pro Lys Gly Lys Ser Glu Gly Glu Val Met
130                 135                 140

Arg Phe Cys Gln Ala Leu Met Thr Glu Leu Tyr Arg His Leu Gly Ala
145                 150                 155                 160

Asp Thr Asp Val Pro Ala Gly Asp Ile Gly Val Gly Gly Arg Glu Val
                165                 170                 175

Gly Phe Met Ala Gly Met Met Lys Lys Leu Ser Asn Asn Thr Ala Cys
            180                 185                 190

Val Phe Thr Gly Lys Gly Leu Ser Phe Gly Gly Ser Leu Ile Arg Pro
        195                 200                 205

Glu Ala Thr Gly Tyr Gly Leu Val Tyr Phe Thr Glu Ala Met Leu Lys
    210                 215                 220

Arg His Gly Met Gly Phe Glu Gly Met Arg Val Ser Val Ser Gly Ser
225                 230                 235                 240

Gly Asn Val Ala Gln Tyr Ala Ile Glu Lys Ala Met Glu Phe Gly Ala
                245                 250                 255

Arg Val Ile Thr Ala Ser Asp Ser Ser Gly Thr Val Val Asp Glu Ser
            260                 265                 270

Gly Phe Thr Lys Glu Lys Leu Ala Arg Leu Ile Glu Ile Lys Ala Ser
        275                 280                 285

Arg Asp Gly Arg Val Ala Asp Tyr Ala Lys Glu Phe Gly Leu Val Tyr
    290                 295                 300

Leu Glu Gly Gln Gln Pro Trp Ser Leu Pro Val Asp Ile Ala Leu Pro
305                 310                 315                 320

Cys Ala Thr Gln Asn Glu Leu Asp Val Asp Ala Ala His Gln Leu Ile
                325                 330                 335

Ala Asn Gly Val Lys Ala Val Ala Glu Gly Ala Asn Met Pro Thr Thr
```

```
                    340                 345                 350
Ile Glu Ala Thr Glu Leu Phe Gln Gln Ala Gly Val Leu Phe Ala Pro
            355                 360                 365

Gly Lys Ala Ala Asn Ala Gly Val Ala Thr Ser Gly Leu Glu Met
        370                 375                 380

Ala Gln Asn Ala Ala Arg Leu Gly Trp Lys Ala Glu Lys Val Asp Ala
385                 390                 395                 400

Arg Leu His His Ile Met Leu Asp Ile His His Ala Cys Val Glu His
                405                 410                 415

Gly Gly Glu Gly Glu Gln Thr Asn Tyr Val Gln Gly Ala Asn Ile Ala
            420                 425                 430

Gly Phe Val Lys Val Ala Asp Ala Met Leu Ala Gln Gly Val Ile
            435                 440                 445

<210> SEQ ID NO 3
<211> LENGTH: 447
<212> TYPE: PRT
<213> ORGANISM: Escherichia coli

<400> SEQUENCE: 3

Met Asp Gln Thr Tyr Ser Leu Glu Ser Phe Leu Asn His Val Gln Lys
1               5                   10                  15

Arg Asp Pro Asn Gln Thr Glu Phe Ala Gln Ala Val Arg Glu Val Met
            20                  25                  30

Thr Thr Leu Trp Pro Phe Leu Glu Gln Asn Pro Lys Tyr Arg Gln Met
        35                  40                  45

Ser Leu Leu Glu Arg Leu Val Glu Pro Glu Arg Val Ile Gln Phe Arg
    50                  55                  60

Val Val Trp Val Asp Asp Arg Asn Gln Ile Gln Val Asn Arg Ala Trp
65                  70                  75                  80

Arg Val Gln Phe Ser Ser Ala Ile Gly Pro Tyr Val Gly Gly Met Arg
                85                  90                  95

Phe His Pro Ser Val Asn Leu Ser Ile Leu Lys Phe Leu Gly Phe Glu
            100                 105                 110

Gln Thr Phe Lys Asn Ala Leu Thr Thr Leu Pro Met Gly Gly Gly Lys
        115                 120                 125

Gly Gly Ser Asp Phe Asp Pro Lys Gly Lys Ser Glu Gly Glu Val Met
    130                 135                 140

Arg Phe Cys Gln Ala Leu Met Thr Glu Leu Tyr Arg His Leu Gly Ala
145                 150                 155                 160

Asp Thr Asp Val Pro Ala Gly Asp Ile Gly Val Gly Gly Arg Glu Val
                165                 170                 175

Gly Phe Met Ala Gly Met Met Lys Lys Leu Ser Asn Asn Thr Ala Cys
            180                 185                 190

Val Phe Ser Gly Lys Gly Leu Ser Phe Gly Gly Ser Leu Ile Arg Pro
        195                 200                 205

Glu Ala Thr Gly Tyr Gly Leu Val Tyr Phe Thr Glu Ala Met Leu Lys
    210                 215                 220

Arg His Gly Met Gly Phe Glu Gly Met Arg Val Ser Val Ser Gly Ser
225                 230                 235                 240

Gly Asn Val Ala Gln Tyr Ala Ile Glu Lys Ala Met Glu Phe Gly Ala
                245                 250                 255

Arg Val Ile Thr Ala Ser Asp Ser Ser Gly Thr Val Val Asp Glu Ser
            260                 265                 270
```

-continued

```
Gly Phe Thr Lys Glu Lys Leu Ala Arg Leu Ile Glu Ile Lys Ala Ser
            275                 280                 285

Arg Asp Gly Arg Val Ala Asp Tyr Ala Lys Glu Phe Gly Leu Val Tyr
290                 295                 300

Leu Glu Gly Gln Gln Pro Trp Ser Leu Pro Val Asp Ile Ala Leu Pro
305                 310                 315                 320

Cys Ala Thr Gln Asn Glu Leu Asp Val Asp Ala Ala His Gln Leu Ile
                325                 330                 335

Ala Asn Gly Val Lys Ala Val Ala Glu Gly Ala Asn Met Pro Thr Thr
            340                 345                 350

Ile Glu Ala Thr Glu Leu Phe Gln Gln Ala Gly Val Leu Phe Ala Pro
        355                 360                 365

Gly Lys Ala Ala Asn Ala Gly Gly Val Ala Thr Ser Gly Leu Glu Met
    370                 375                 380

Ala Gln Asn Ala Ala Arg Leu Gly Trp Lys Ala Glu Lys Val Asp Ala
385                 390                 395                 400

Arg Leu His His Ile Met Leu Asp Ile His His Ala Cys Val Glu His
                405                 410                 415

Gly Gly Glu Gly Glu Gln Thr Asn Tyr Val Gln Gly Ala Asn Ile Ala
            420                 425                 430

Gly Phe Val Lys Val Ala Asp Ala Met Leu Ala Gln Gly Val Ile
        435                 440                 445

<210> SEQ ID NO 4
<211> LENGTH: 424
<212> TYPE: PRT
<213> ORGANISM: Bacillus subtilis

<400> SEQUENCE: 4

Met Ser Ala Lys Gln Val Ser Lys Asp Glu Glu Lys Glu Ala Leu Asn
1               5                   10                  15

Leu Phe Leu Ser Thr Gln Thr Ile Ile Lys Glu Ala Leu Arg Lys Leu
            20                  25                  30

Gly Tyr Pro Gly Asp Met Tyr Glu Leu Met Lys Glu Pro Gln Arg Met
        35                  40                  45

Leu Thr Val Arg Ile Pro Val Lys Met Asp Asn Gly Ser Val Lys Val
50                  55                  60

Phe Thr Gly Tyr Arg Ser Gln His Asn Asp Ala Val Gly Pro Thr Lys
65                  70                  75                  80

Gly Gly Val Arg Phe His Pro Glu Val Asn Glu Glu Val Lys Ala
            85                  90                  95

Leu Ser Ile Trp Met Thr Leu Lys Cys Gly Ile Ala Asn Leu Pro Tyr
            100                 105                 110

Gly Gly Gly Lys Gly Gly Ile Ile Cys Asp Pro Arg Thr Met Ser Phe
        115                 120                 125

Gly Glu Leu Glu Arg Leu Ser Arg Gly Tyr Val Arg Ala Ile Ser Gln
    130                 135                 140

Ile Val Gly Pro Thr Lys Asp Ile Pro Ala Pro Asp Val Tyr Thr Asn
145                 150                 155                 160

Ser Gln Ile Met Ala Trp Met Met Asp Glu Tyr Ser Arg Leu Arg Glu
                165                 170                 175

Phe Asp Ser Pro Gly Phe Ile Thr Gly Lys Pro Leu Val Leu Gly Gly
            180                 185                 190

Ser Gln Gly Arg Glu Thr Ala Thr Ala Gln Gly Val Thr Ile Cys Ile
        195                 200                 205
```

Glu Glu Ala Val Lys Lys Gly Ile Lys Leu Gln Asn Ala Arg Ile
        210                 215                 220

Ile Ile Gln Gly Phe Gly Asn Ala Gly Ser Phe Leu Ala Lys Phe Met
225                 230                 235                 240

His Asp Ala Gly Ala Lys Val Ile Gly Ile Ser Asp Ala Asn Gly Gly
                    245                 250                 255

Leu Tyr Asn Pro Asp Gly Leu Asp Ile Pro Tyr Leu Leu Asp Lys Arg
                260                 265                 270

Asp Ser Phe Gly Met Val Thr Asn Leu Phe Thr Asp Val Ile Thr Asn
            275                 280                 285

Glu Glu Leu Leu Glu Lys Asp Cys Asp Ile Leu Val Pro Ala Ala Ile
        290                 295                 300

Ser Asn Gln Ile Thr Ala Lys Asn Ala His Asn Ile Gln Ala Ser Ile
305                 310                 315                 320

Val Val Glu Ala Ala Asn Gly Pro Thr Thr Ile Asp Ala Thr Lys Ile
                    325                 330                 335

Leu Asn Glu Arg Gly Val Leu Leu Val Pro Asp Ile Leu Ala Ser Ala
                340                 345                 350

Gly Gly Val Thr Val Ser Tyr Phe Glu Trp Val Gln Asn Asn Gln Gly
            355                 360                 365

Tyr Tyr Trp Ser Glu Glu Val Ala Glu Lys Leu Ser Asn Val Met
        370                 375                 380

Val Ser Ser Phe Glu Thr Ile Tyr Gln Thr Ala Ala Thr His Lys Val
385                 390                 395                 400

Asp Met Arg Leu Ala Ala Tyr Met Thr Gly Ile Arg Lys Ser Ala Glu
                405                 410                 415

Ala Ser Arg Phe Arg Gly Trp Val
            420

<210> SEQ ID NO 5
<211> LENGTH: 424
<212> TYPE: PRT
<213> ORGANISM: Bacillus subtilis

<400> SEQUENCE: 5

Met Ser Ala Lys Gln Val Ser Lys Asp Glu Glu Lys Glu Ala Leu Asn
1               5                   10                  15

Leu Phe Leu Ser Thr Gln Thr Ile Ile Lys Glu Ala Leu Arg Lys Leu
                20                  25                  30

Gly Tyr Pro Gly Asp Met Tyr Glu Leu Met Lys Glu Pro Gln Arg Met
            35                  40                  45

Leu Thr Val Arg Ile Pro Val Lys Met Asp Asn Gly Ser Val Lys Val
50                  55                  60

Phe Thr Gly Tyr Arg Ser Gln His Asn Asp Ala Val Gly Pro Thr Val
65                  70                  75                  80

Gly Gly Val Arg Phe His Pro Glu Val Asn Glu Glu Val Lys Ala
                    85                  90                  95

Leu Ser Ile Trp Met Thr Leu Lys Cys Gly Ile Ala Asn Leu Pro Tyr
                100                 105                 110

Gly Gly Gly Lys Gly Gly Ile Ile Cys Asp Pro Arg Thr Met Ser Phe
            115                 120                 125

Gly Glu Leu Glu Arg Leu Ser Arg Gly Tyr Val Arg Ala Ile Ser Gln
        130                 135                 140

Ile Val Gly Pro Thr Lys Asp Ile Pro Ala Pro Asp Val Tyr Thr Asn

```
                145                 150                 155                 160
Ser Gln Ile Met Ala Trp Met Met Asp Glu Tyr Ser Arg Leu Arg Glu
                165                 170                 175

Phe Asp Ser Pro Gly Phe Ile Thr Gly Lys Pro Leu Val Leu Gly Gly
            180                 185                 190

Ser Gln Gly Arg Glu Thr Ala Thr Ala Gln Gly Val Thr Ile Cys Ile
            195                 200                 205

Glu Glu Ala Val Lys Lys Gly Ile Lys Leu Gln Asn Ala Arg Ile
    210                 215                 220

Ile Ile Gln Gly Phe Gly Asn Ala Gly Ser Phe Leu Ala Lys Phe Met
225                 230                 235                 240

His Asp Ala Gly Ala Lys Val Ile Gly Ile Ser Asp Ala Asn Gly Gly
                245                 250                 255

Leu Tyr Asn Pro Asp Gly Leu Asp Ile Pro Tyr Leu Leu Asp Lys Arg
            260                 265                 270

Asp Ser Phe Gly Met Val Thr Asn Leu Phe Thr Asp Val Ile Thr Asn
            275                 280                 285

Glu Glu Leu Leu Glu Lys Asp Cys Asp Ile Leu Val Pro Ala Ala Ile
    290                 295                 300

Ser Asn Gln Ile Thr Ala Lys Asn Ala His Asn Ile Gln Ala Ser Ile
305                 310                 315                 320

Val Val Glu Ala Ala Asn Gly Pro Thr Thr Ile Asp Ala Thr Lys Ile
                325                 330                 335

Leu Asn Glu Arg Gly Val Leu Leu Val Pro Asp Ile Leu Ala Ser Ala
            340                 345                 350

Gly Gly Val Thr Val Ser Tyr Phe Glu Trp Val Gln Asn Asn Gln Gly
            355                 360                 365

Tyr Tyr Trp Ser Glu Glu Glu Val Ala Glu Lys Leu Ser Asn Val Met
        370                 375                 380

Val Ser Ser Phe Glu Thr Ile Tyr Gln Thr Ala Ala Thr His Lys Val
385                 390                 395                 400

Asp Met Arg Leu Ala Ala Tyr Met Thr Gly Ile Arg Lys Ser Ala Glu
                405                 410                 415

Ala Ser Arg Phe Arg Gly Trp Val
            420

<210> SEQ ID NO 6
<211> LENGTH: 424
<212> TYPE: PRT
<213> ORGANISM: Bacillus subtilis

<400> SEQUENCE: 6

Met Ser Ala Lys Gln Val Ser Lys Asp Glu Glu Lys Glu Ala Leu Asn
1               5                   10                  15

Leu Phe Leu Ser Thr Gln Thr Ile Ile Lys Glu Ala Leu Arg Lys Leu
            20                  25                  30

Gly Tyr Pro Gly Asp Met Tyr Glu Leu Met Lys Glu Pro Gln Arg Met
        35                  40                  45

Leu Thr Val Arg Ile Pro Val Lys Met Asp Asn Gly Ser Val Lys Val
    50                  55                  60

Phe Thr Gly Tyr Arg Ser Gln His Asn Asp Ala Val Gly Pro Thr Val
65                  70                  75                  80

Gly Gly Val Arg Phe His Pro Glu Val Asn Glu Glu Glu Val Lys Ala
            85                  90                  95
```

-continued

Leu Ser Ile Trp Met Thr Leu Lys Cys Gly Ile Ala Asn Leu Pro Tyr
                100                 105                 110

Gly Gly Gly Lys Gly Ile Ile Cys Asp Pro Arg Thr Met Ser Phe
        115                 120                 125

Gly Glu Leu Glu Arg Leu Ser Arg Gly Tyr Val Arg Ala Ile Ser Gln
    130                 135                 140

Ile Val Gly Pro Thr Lys Asp Ile Pro Ala Pro Asp Val Tyr Thr Asn
145                 150                 155                 160

Ser Gln Ile Met Ala Trp Met Met Asp Glu Tyr Ser Arg Leu Arg Glu
                165                 170                 175

Phe Asp Ser Pro Gly Phe Ile Ser Gly Lys Pro Leu Val Leu Gly Gly
            180                 185                 190

Ser Gln Gly Arg Glu Thr Ala Thr Ala Gln Gly Val Thr Ile Cys Ile
        195                 200                 205

Glu Glu Ala Val Lys Lys Gly Ile Lys Leu Gln Asn Ala Arg Ile
    210                 215                 220

Ile Ile Gln Gly Phe Gly Asn Ala Gly Ser Phe Leu Ala Lys Phe Met
225                 230                 235                 240

His Asp Ala Gly Ala Lys Val Ile Gly Ile Ser Asp Ala Asn Gly Gly
                245                 250                 255

Leu Tyr Asn Pro Asp Gly Leu Asp Ile Pro Tyr Leu Leu Asp Lys Arg
            260                 265                 270

Asp Ser Phe Gly Met Val Thr Asn Leu Phe Thr Asp Val Ile Thr Asn
        275                 280                 285

Glu Glu Leu Leu Glu Lys Asp Cys Asp Ile Leu Val Pro Ala Ala Ile
    290                 295                 300

Ser Asn Gln Ile Thr Ala Lys Asn Ala His Asn Ile Gln Ala Ser Ile
305                 310                 315                 320

Val Val Glu Ala Ala Asn Gly Pro Thr Thr Ile Asp Ala Thr Lys Ile
                325                 330                 335

Leu Asn Glu Arg Gly Val Leu Leu Val Pro Asp Ile Leu Ala Ser Ala
            340                 345                 350

Gly Gly Val Thr Val Ser Tyr Phe Glu Trp Val Gln Asn Asn Gln Gly
        355                 360                 365

Tyr Tyr Trp Ser Glu Glu Val Ala Glu Lys Leu Ser Asn Val Met
370                 375                 380

Val Ser Ser Phe Glu Thr Ile Tyr Gln Thr Ala Ala Thr His Lys Val
385                 390                 395                 400

Asp Met Arg Leu Ala Ala Tyr Met Thr Gly Ile Arg Lys Ser Ala Glu
            405                 410                 415

Ala Ser Arg Phe Arg Gly Trp Val
            420

<210> SEQ ID NO 7
<211> LENGTH: 38
<212> TYPE: DNA
<213> ORGANISM: Artificial Sequence
<220> FEATURE:
<223> OTHER INFORMATION: Primer gdh_F

<400> SEQUENCE: 7
cagccatatg gatcagacat attctctgga gtcattcc          38

<210> SEQ ID NO 8
<211> LENGTH: 31
<212> TYPE: DNA

```
<213> ORGANISM: Artificial Sequence
<220> FEATURE:
<223> OTHER INFORMATION: Primer gdh_R

<400> SEQUENCE: 8
atatgtcgac ttaaatcaca ccctgcgcca g                              31

<210> SEQ ID NO 9
<211> LENGTH: 29
<212> TYPE: DNA
<213> ORGANISM: Artificial Sequence
<220> FEATURE:
<223> OTHER INFORMATION: Primer pdc_F

<400> SEQUENCE: 9
cagccatatg agttatactg tcggtacct                                 29

<210> SEQ ID NO 10
<211> LENGTH: 53
<212> TYPE: DNA
<213> ORGANISM: Artificial Sequence
<220> FEATURE:
<223> OTHER INFORMATION: Primer pdc_R

<400> SEQUENCE: 10
attaaagctt ctagtggtgg tggtggtggt ggaggagctt gttaacaggc tta      53

<210> SEQ ID NO 11
<211> LENGTH: 31
<212> TYPE: DNA
<213> ORGANISM: Artificial Sequence
<220> FEATURE:
<223> OTHER INFORMATION: Primer kdc_F

<400> SEQUENCE: 11
cagccatatg tataccgtgg gtgattatct g                              31

<210> SEQ ID NO 12
<211> LENGTH: 51
<212> TYPE: DNA
<213> ORGANISM: Artificial Sequence
<220> FEATURE:
<223> OTHER INFORMATION: Primer kdc_R

<400> SEQUENCE: 12
attaaagctt ctagtggtgg tggtggtggt gtttgttctg ctcggcaaac a        51

<210> SEQ ID NO 13
<211> LENGTH: 56
<212> TYPE: DNA
<213> ORGANISM: Artificial Sequence
<220> FEATURE:
<223> OTHER INFORMATION: Primer yqhD_F

<400> SEQUENCE: 13
attaaagctt aactttaaga aggagatata cagatgaaca actttaatct gcacac   56

<210> SEQ ID NO 14
<211> LENGTH: 30
<212> TYPE: DNA
<213> ORGANISM: Artificial Sequence
<220> FEATURE:
<223> OTHER INFORMATION: Primer yqhD_R

<400> SEQUENCE: 14
attactcgag gcgggcggct tcgtatatac                                30
```

<210> SEQ ID NO 15
<211> LENGTH: 31
<212> TYPE: DNA
<213> ORGANISM: Artificial Sequence
<220> FEATURE:
<223> OTHER INFORMATION: Primer K92Q

<400> SEQUENCE: 15
ccatcggccc gtaccagggc ggtatgcgct t                                      31

<210> SEQ ID NO 16
<211> LENGTH: 31
<212> TYPE: DNA
<213> ORGANISM: Artificial Sequence
<220> FEATURE:
<223> OTHER INFORMATION: Primer K92Q_antisense

<400> SEQUENCE: 16
aagcgcatac cgccctggta cgggccgatg g                                      31

<210> SEQ ID NO 17
<211> LENGTH: 31
<212> TYPE: DNA
<213> ORGANISM: Artificial Sequence
<220> FEATURE:
<223> OTHER INFORMATION: Primer S380Q

<400> SEQUENCE: 17
tgctggtggc gtcgctacac agggcctgga a                                      31

<210> SEQ ID NO 18
<211> LENGTH: 31
<212> TYPE: DNA
<213> ORGANISM: Artificial Sequence
<220> FEATURE:
<223> OTHER INFORMATION: Primer S380Q_antisense

<400> SEQUENCE: 18
ttccaggccc tgtgtagcga cgccaccagc a                                      31

<210> SEQ ID NO 19
<211> LENGTH: 26
<212> TYPE: DNA
<213> ORGANISM: Artificial Sequence
<220> FEATURE:
<223> OTHER INFORMATION: Primer T195S

<400> SEQUENCE: 19
ccgcctgcgt cttcagcggt aagggc                                            26

<210> SEQ ID NO 20
<211> LENGTH: 26
<212> TYPE: DNA
<213> ORGANISM: Artificial Sequence
<220> FEATURE:
<223> OTHER INFORMATION: Primer T195S_antisense

<400> SEQUENCE: 20
gcccttaccg ctgaagacgc aggcgg                                            26

<210> SEQ ID NO 21
<211> LENGTH: 30
<212> TYPE: DNA
<213> ORGANISM: Artificial Sequence
<220> FEATURE:

<223> OTHER INFORMATION: Primer K92V

<400> SEQUENCE: 21
ccatcggccc gtacgtaggc ggtatgcgct                                30

<210> SEQ ID NO 22
<211> LENGTH: 30
<212> TYPE: DNA
<213> ORGANISM: Artificial Sequence
<220> FEATURE:
<223> OTHER INFORMATION: Primer K92V_antisense

<400> SEQUENCE: 22
agcgcatacc gcctacgtac gggccgatgg                                30

<210> SEQ ID NO 23
<211> LENGTH: 41
<212> TYPE: DNA
<213> ORGANISM: Artificial Sequence
<220> FEATURE:
<223> OTHER INFORMATION: Primer T195Q

<400> SEQUENCE: 23
caataccgcc tgcgtcttcc agggtaaggg cctttcattt g                   41

<210> SEQ ID NO 24
<211> LENGTH: 41
<212> TYPE: DNA
<213> ORGANISM: Artificial Sequence
<220> FEATURE:
<223> OTHER INFORMATION: Primer T195Q_antisense

<400> SEQUENCE: 24
caaatgaaag gcccttaccc tggaagacgc aggcggtatt g                   41

<210> SEQ ID NO 25
<211> LENGTH: 31
<212> TYPE: DNA
<213> ORGANISM: Artificial Sequence
<220> FEATURE:
<223> OTHER INFORMATION: Primer K92M

<400> SEQUENCE: 25
ctgccatcgg cccgtacatg ggcggtatgc g                              31

<210> SEQ ID NO 26
<211> LENGTH: 31
<212> TYPE: DNA
<213> ORGANISM: Artificial Sequence
<220> FEATURE:
<223> OTHER INFORMATION: Primer K92M_antisense

<400> SEQUENCE: 26
cgcataccgc ccatgtacgg gccgatggca g                              31

<210> SEQ ID NO 27
<211> LENGTH: 39
<212> TYPE: DNA
<213> ORGANISM: Artificial Sequence
<220> FEATURE:
<223> OTHER INFORMATION: Primer S380N

<400> SEQUENCE: 27
ctaatgctgg tggcgtcgct acaaatggcc tggaaatgg                      39

<210> SEQ ID NO 28
<211> LENGTH: 39
<212> TYPE: DNA
<213> ORGANISM: Artificial Sequence
<220> FEATURE:
<223> OTHER INFORMATION: Primer S380N_antisense

<400> SEQUENCE: 28
ccatttccag gccatttgta gcgacgccac cagcattag                                39

<210> SEQ ID NO 29
<211> LENGTH: 44
<212> TYPE: DNA
<213> ORGANISM: Artificial Sequence
<220> FEATURE:
<223> OTHER INFORMATION: Primer V377L_S380N

<400> SEQUENCE: 29
ggctaatgct ggtggcctcg ctacaaatgg cctggaaatg gcac                          44

<210> SEQ ID NO 30
<211> LENGTH: 44
<212> TYPE: DNA
<213> ORGANISM: Artificial Sequence
<220> FEATURE:
<223> OTHER INFORMATION: Primer V377L_S380N_antisense

<400> SEQUENCE: 30
gtgccatttc caggccattt gtagcgaggc caccagcatt agcc                          44

<210> SEQ ID NO 31
<211> LENGTH: 32
<212> TYPE: DNA
<213> ORGANISM: Artificial Sequence
<220> FEATURE:
<223> OTHER INFORMATION: Primer T195V

<400> SEQUENCE: 31
accgcctgcg tcttcgtcgg taagggcctt tc                                       32

<210> SEQ ID NO 32
<211> LENGTH: 32
<212> TYPE: DNA
<213> ORGANISM: Artificial Sequence
<220> FEATURE:
<223> OTHER INFORMATION: Primer T195V_antisense

<400> SEQUENCE: 32
gaaaggccct taccgacgaa gacgcaggcg gt                                       32

<210> SEQ ID NO 33
<211> LENGTH: 51
<212> TYPE: DNA
<213> ORGANISM: Artificial Sequence
<220> FEATURE:
<223> OTHER INFORMATION: Primer kdcA_F

<400> SEQUENCE: 33
gaggagaaag gtaccaactt taagaaggag atatacatat gtataccgtg g                  51

<210> SEQ ID NO 34
<211> LENGTH: 42
<212> TYPE: DNA
<213> ORGANISM: Artificial Sequence
<220> FEATURE:
<223> OTHER INFORMATION: Primer kdcA _R

```
<400> SEQUENCE: 34
ttatttgttc tgctcggcaa acagtttacc catttttttc ag                          42

<210> SEQ ID NO 35
<211> LENGTH: 61
<212> TYPE: DNA
<213> ORGANISM: Artificial Sequence
<220> FEATURE:
<223> OTHER INFORMATION: Primer yqhD_F2

<400> SEQUENCE: 35
gagcagaaca aataaaactt taagaaggag atatacatat gaacaacttt aatctgcaca       60
c                                                                       61

<210> SEQ ID NO 36
<211> LENGTH: 35
<212> TYPE: DNA
<213> ORGANISM: Artificial Sequence
<220> FEATURE:
<223> OTHER INFORMATION: Primer yqhD_R2

<400> SEQUENCE: 36
atgcctctag agtcattagc gggcggcttc gtata                                  35

<210> SEQ ID NO 37
<211> LENGTH: 31
<212> TYPE: DNA
<213> ORGANISM: Artificial Sequence
<220> FEATURE:
<223> OTHER INFORMATION: Primer pZA_F

<400> SEQUENCE: 37
tgactctaga ggcatcaaat aaaacgaaag g                                      31

<210> SEQ ID NO 38
<211> LENGTH: 31
<212> TYPE: DNA
<213> ORGANISM: Artificial Sequence
<220> FEATURE:
<223> OTHER INFORMATION: Primer pZA_R

<400> SEQUENCE: 38
ggtacctttc tcctctttaa tgaattcggt c                                      31

<210> SEQ ID NO 39
<211> LENGTH: 46
<212> TYPE: DNA
<213> ORGANISM: Artificial Sequence
<220> FEATURE:
<223> OTHER INFORMATION: Primer gdh_F2

<400> SEQUENCE: 39
ttaaagagga gaaagacata tggatcagac atattctctg gagtca                      46

<210> SEQ ID NO 40
<211> LENGTH: 37
<212> TYPE: DNA
<213> ORGANISM: Artificial Sequence
<220> FEATURE:
<223> OTHER INFORMATION: Primer gdh_R2

<400> SEQUENCE: 40
tccttcttaa agttgttaaa tcacaccctg cgccagc                                37
```